United States Patent [19]

Grimsley et al.

[11] Patent Number: 5,569,597

[45] Date of Patent: Oct. 29, 1996

[54] METHODS OF INSERTING VIRAL DNA INTO PLANT MATERIAL

[75] Inventors: Nigel H. Grimsley, Saint Léon, France; Barbara Hohn; Thomas Hohn, both of Arlesheim, Switzerland; Jeffrey W. Davies, Norwich; Margaret I. Boulton, Dereham, both of England

[73] Assignees: Ciba Geigy Corp., Ardsley, N.Y.; Mycogen Plant Sciences, Inc., San Diego, Calif.

[21] Appl. No.: 272,958

[22] Filed: Jul. 11, 1994

Related U.S. Application Data

[63] Continuation of Ser. No. 966,248, Oct. 26, 1992, abandoned, and a continuation-in-part of Ser. No. 798,859, Nov. 22, 1991, abandoned, which is a continuation of Ser. No. 526,949, May 22, 1990, abandoned, which is a continuation of Ser. No. 211,080, Jun. 21, 1988, abandoned, which is a continuation of Ser. No. 859,682, May 5, 1986, abandoned, said Ser. No. 966,248, is a continuation-in-part of Ser. No. 497,799, Mar. 22, 1990, abandoned, which is a continuation of Ser. No. 118,094, Nov. 5, 1987, abandoned.

[30] Foreign Application Priority Data

May 13, 1985 [CH] Switzerland ............................ 2026/85
Nov. 7, 1986 [CH] Switzerland ............................ 4456/86
Jun. 16, 1987 [CH] Switzerland ............................ 2255/87

[51] Int. Cl.⁶ .............................. C12N 15/00; C12N 15/05
[52] U.S. Cl. .................... 435/172.3; 435/172.1; 435/320.1; 935/52; 935/56; 935/57; 800/205
[58] Field of Search ........................... 435/172.1, 172.3, 435/240.4, 240.45, 240.49, 320.1; 935/52, 56, 57

[56] References Cited

U.S. PATENT DOCUMENTS 5,177,010  1/1993  Goldman et al. .................... 435/172.3
5,187,073  2/1993  Goldman et al. .................... 435/172.3

FOREIGN PATENT DOCUMENTS 0193259  9/1986  European Pat. Off. ........ C12N 15/00

OTHER PUBLICATIONS

Hooykas–Van Slogteren et al. (1984) Expression of Ti plasmid genes in momocotyledonous infected with *Agrobacterium tumefaciens*. Nature vol. 311 pp. 763–764.
Graves et al. (1986) The transformation of *Zea mays* seedlings with *Agrobacterium tumefaciens*. Plant Molecular Biology vol. 7 pp. 43–50.
Abel et al. (1986) Delay of disease development in transgenic plants that express the tobacco mosaic virus coat protein gene. Science vol. 232, pp. 738–743.
Stachel et al. (1985) Nature vol. 318 pp. 624–629.
Nelson et al. (1987) Virology vol. 158 pp. 126–132.
Grinsley et al. (1986) PNAS vol. 83 pp. 3282–3286.
Barton et al (1987) Plant Physiology vol. 85 pp. 1103–1109.
Hernalsteens et al (1984) The EMBO vol. 3 #13, pp. 3039–3039.
Sheumaker (1985) Virology vol. 140 pp. 281–288.
Lebeurier et al (1982) PNAS vol. 79 pp. 2932–2936.

*Primary Examiner*—Gary Benzion
*Attorney, Agent, or Firm*—Saliwanchik & Saliwanchik

[57] ABSTRACT

The present invention relates to a novel method of inserting viral DNA, which optionally may contain cargo-DNA, into plants or viable parts thereof, but preferably into plants of the monocotyledon class, and most preferably into plants of the family Gramineae, using suitable transfer microorganisms. Further comprised by the invention are recombinant DNA, plasmid and vector molecules suitably adapted to the specific conditions of the process according to the invention and the transgenic plant products obtainable in accordance with the said process.

43 Claims, 1 Drawing Sheet

METHODS OF INSERTING VIRAL DNA INTO PLANT MATERIAL

This application is a continuation, of application Ser. No. 07/966,248 Oct. 26, 1992 now abandoned, which is a continuation-in-part of 07/497,799 filed on Mar. 22, 1990, now abandoned, which is a continuation of 07/118,094 filed Nov. 5, 1987, now abandoned, and a continuation-in-part of 07/798,859 filed Nov. 22, 1991, now abandoned, which is a continuation of 07/526,949 filed May 22, 1990, now abandoned, which is a continuation of 07/211,080 filed Jun. 21,1988, now abandoned, which is a continuation of 06/859,682 filed May 5, 1986, now abandoned.

BACKGROUND OF THE INVENTION

The present invention relates to a novel method of inserting vital DNA, which optionally may contain cargo-DNA, into plants or viable parts thereof, but preferably into plants of the monocotyledon class, and most preferably into plants of the family Gramineae, using suitable transfer microorganisms. Further comprised by the invention are recombinant DNA, plasmid and vector molecules suitably adapted to the specific conditions of the process according to the invention and the transgenic plant products obtainable in accordance with the said process.

In view of the rapid increase in world population and the associated greater need for foodstuffs and raw materials, increasing the yield of useful plants and also increased extraction of plant contents, that is to say progress in the field of foodstuffs and medicines, is one of the most urgent tasks of biological and biotechnological research. In this connection, for example the following should be mentioned as essential aspects: increasing the resistance of useful plants to diseases and pests or to unfavourable soil conditions, increasing resistance to plant-protecting agents such as insecticides, herbicides, fungicides and bactericides, and beneficially modifying the nutrient content or the yield of plants. Such desirable effects could in general be brought about by induction or increased formation of protective substances, valuable proteins or toxins and by interventions in the regulatory system of plant metabolism. Influencing the plant genotype appropriately can be effected, for example, by transferring new genes into whole plants or into plant cells.

It has already proved possible in many cases to insert selected DNA fragments into viral DNA and then, together with the virus, to introduce them into another organism. Although most plant viruses are transmitted under natural conditions by insects that feed on infected and uninfected plants, thereby causing fresh infection of plants, this route is too inconvenient and difficult to control to achieve a selective and systematic transmission of viruses. Thus, for example, specially bred insect populations would be required for such a method under contained conditions. In addition, it would be very difficult to achieve a controlled virus infection, especially of large amounts of plant material.

The mechanical inoculation of leaves with viruses, the method so far employed in genetic engineering, is of only limited applicability, as cloned viral DNA is commonly believed to be non-infectious.

Although it is possible to clone and study in bacteria a variety of types of vital genomes, for example single stranded DNA viruses which are obtained by cloning double-stranded DNA forms [Mullineaux, P.M. et al, 1984], many viruses that are cloned in bacteria cannot be reintroduced into plants or used for infecting plants. The use of methods such as in vitro mutagenesis and recombinant DNA technology are therefore ruled out in basic studies as well as for exploiting such viruses as carriers of selected foreign DNA. Such problems do not arise when using the method of this invention as set forth hereinbelow.

Prior to the present invention there have been only a few reports concerning the introduction of cloned viral DNA into plant cells.

Howell et al (1980), for example, describe infection of turnip plants by cloned CaMV DNA. It is specifically emphasized in the said reference that the cloned viral DNA must be excised from the recombinant plasmid before it is capable of infecting the turnip plants.

Lebeurier et al (1982) demonstrate that a cloned tandem dimer of CaMV DNA with a partial deletion is infectious in a plant assay. The vital genome was inoculated as part of a pBR322 double-stranded DNA plasmid by artificial leaf inoculation.

Lebeurier et al do not teach introduction of a tandemly duplicated CaMV genome into the plant cell as part of an Agrobacterium Ti-plasmid using the Agrobacterium transformation system.

Cress et al (1983) demonstrate that dimeric PSTV cDNA is infectious in a plant assay when inoculated by artificial means as part of a recombinant bacterial plasmid. Again, Cress et al do not teach use of the Agrobacterium system as an alternative route for delivering the vital DNA into the plant cell.

Prior to the present invention the only mentioning of vital DNA in connection with the Agrobacterium transformation system can be found in U.S. Pat. No. 4,536,475 [Anderson] and Shewmaker et al (1985)

Anderson [U.S. Pat. No. 4,536,475] discloses a variety of recombinant plasmid molecules which comprise a bacterial plasmid into which are ligated the border sequences from the T-DNA regions of the Ti-plasmid of *Agrobacterium tumefaciens*. Anderson teach that the CaMV DNA can be employed as a DNA source of an eucaryotic origin of replication, which was considered helpful in increasing the opportunity for integration of the introduced DNA to occur.

Accordingly, Anderson disclose CaMV DNA sequences that are situated outside of the the T-DNA and thus have not been assigned for the introduction into the plant cell's genome.

Shewmaker et al (1985), on the other side, describe experiments in which a full-length copy of CaMV is introduced into plant cells using a Ti-plasmid of *Agrobacterium tumefaciens*. However, within the genetic construct used by Shewmaker et al (1985) the full-length viral genome is broken in two places and could thus not give rise to viral infection. Accordingly, by the above experiments Shewmaker et al (1985) were only able to demonstrate that the introduced CaMV genome gave rise to two polyadenylation transcripts. The teaching of Shewmaker et al is thus confined to a showing that the two major promoters of the CaMV genome are supposedly able to function in plant cells.

The above short discussion of the cited references shows that the prior art teaches essentially two different experimental approaches.

The objective of the main approach, which is represented by the Lebeurier et al (1982), the Cress et al (1983), and the Howell et al (1980) reference, is to develop a plant viral transformation system which shall make use of the specific properties of infectious plant virus particles. To achieve this objective, either the cloned viral DNA is excised from the recombinant bacterial plasmid prior to infecting the plant material [Howell et al (1980); Cress et al (1983)], or the whole recombinant plasmid containing duplicated vital copies, which proved able to become recombined out in the plant cell, is introduced into the plant by artificial means [Lebeurier et al (1983)].

However, using the above roughly sketched experimental approach for developing a virus-based plant transformation system would not help to overcome the disadvantages which are involved in a pure viral vector system.

The second experimental approach, which is represented by Shewmaker et al (1983) and by U.S. Pat. No. 4,536,475 [Anderson], relates to studies for establishing novel, improved Ti-plasmid based vector systems, for example by use of plant vital regulatory DNA sequences, such as the two CaMV promoters described in Shewmaker et al (1983), or of the CaMV replication origin as described in U.S. Pat. No. 4,536,475 [Anderson].

Neither Shewmaker et al (1983) nor U.S. Pat. No. 4,536,475 [Anderson] teach the introduction of a complete, intact viral genome, which is capable of giving rise to a functional virus particle in the transformed plant.

SUMMARY OF THE INVENTION

Thus, it was one of the main objectives of the instant invention to provide a method for reintroducing cloned vital DNA, that is normally not infectious upon mechanical inoculation of plant material, into plants.

Within the scope of the present invention it was surprisingly found that in order to achieve this object the two principle experimental approaches discussed hereinbefore can be suitably combined. By taking a combination of selected and rather simple measures, parts of which were already known, it is possible to accomplish the transfer of a functional viral DNA to a plant.

This finding was very surprising, since it was long known that Agrobacterium-mediated DNA delivery is a very complex process involving complex DNA protein interactions, both on the bacterial and on the plant level, which govern transmission of T-DNA to plant cells. So it is, for example, still not known what the T-DNA intermediates look like.

Agrobacterium carries three genetic components that are required for plant cell transformation. The T-DNA is the mobile DNA element that, unlike other transposable elements, does not encode the products that mediate its transfer. Instead, the Ti plasmid virulence region provides most of the trans-acting products for the DNA transfer to the plant. The third component of the T-DNA transfer process resides in the Agrobacterium chromosome.

The activation of the vir gene expression is followed by several dramatic changes to the T-DNA element on the Ti plasmid that ultimately result in its transfer to the plant cell.

Unlike DNA transfer between bacteria during conjugation, T-DNA must be capable of penetrating the plant cell membrane, localizing and eventually penetrating the nuclear membrane. For this purpose the T-DNA intermediate is expected to have a specific structure, the nature of which is not yet known. A considerable and meanwhile well recognized suggestion in this respect is that single stranded T-DNA intermediates are involved in the T-DNA transfer process [Zambryski A, (1988)], which would not leave any of the known options for the viral DNA to become released.

Therefore, owing to the many imponderabilities involved in DNA delivery via Agrobacterium it was very surprising to find that the concept envisaged by the present invention did actually work.

In particular, the present invention relates to a novel method of introducing cloned viral DNA or functional equivalents thereof, that are normally not infectious upon mechanical inoculation of plants, into plant material of plants that are naturally amenable, or, if not, are made amenable artificially, to transformation by a transfer microorganism such as, for example, a transfer microorganism of the genus Agrobacterium, or viable parts thereof such as, for example, plant cell culture cells, which method comprises essentially the following procedural steps:

a) inserting cloned viral DNA or functional parts thereof, that preferably are capable of giving rise to a systemic infection, and optionally may contain cargo DNA, into a T-replicon, for example a Ti-plasmid or Ri-plasmid of an Agrobacterium, in the vicinity of one or more T-DNA border sequences, the distance between said viral DNA and the T-DNA sequence or sequences being chosen such that viral DNA, including any cargo DNA present, is transferred to plant material;

b) introducing the replicon into a transfer microorganism, for example a microorganism of the genus Agrobacterium; and c) infecting plant material with the transfer microorganism that has been modified in accordance with b).

This method ensures that, after induction of the microbial functions that promote the transfer of the plasmid DNA to plants, the inserted DNA is also transferred, including any cargo DNA that may be present. The transformed plant material so obtained can be regenerated to completely transformed plants.

The said induction process described in detail below may, on the one hand, be triggered by the plant its eft, if suitable culturing and application conditions are applied, the plant being stimulated thereby to synthesize the said inducers itself; or alternatively synthetic or natural inducers such as those provided in formulae I and Ia may be added to the culture medium individually or in combination in a suitable concentration.

In applying the method according to the invention it was further surprisingly found that not only those plants known to be host plants of Agrobacterium could be transformed by the method according to the invention, but also plants belonging to the monocotyledon class and here especially plants of the family Gramineae, which prior to the present invention were commonly believed to be insusceptible to an Agrobacterium infection.

The greatest problem in using recombinant DNA technology in plants from the monocotyledon group resides in the lack of suitable translet microorganisms, with the aid of which transformation frequencies that are sufficiently high for practical application can be achieved and which could thus be used as auxiliaries for a specifically directed insertion into the plant genome. *Agrobacterium tumefaciens*, for example, one of the most used transfer microorganisms for inserting genetic material into plants, is excellently suitable for genetic manipulation of numerous dicotyledonous plants, but so far it has not been possible to achieve correspondingly satisfactory results with representatives of monocotyledons, especially monocotyledonous cultivated plants since, from the monocotyledon class, so far only a few selected families are known that respond to infection with *Agrobacterium tumefaciens* and thus, at least theoretically, might be open to genetic manipulation. These families are, however, from the point of view of agricultural economics, insignificant marginal groups which could at most, be of importance as model plants. [DeCleene M, 1985; Hemalsteens JP et al, 1984; Hooykaas-Van Slogteren GMS et al, 1984; Graves ACF and Goldman SL, 1987].

It is precisely the Gramineae family, however, which includes the cultivated plants that are the most important from the point of view of agricultural economics including our most important types of cereal, such as, for example, wheat, barley, rye, oats, maize, rice, millet, inter alia, which are of particular exonomic interest, so that the development of processes that make it possible, irrespective of the above-mentioned limitations, also to make Gramineae representatives open to direct genetic modification must be regarded as an urgent problem.

The present invention thus preferably relates to a method of introducing cloned viral DNA, that optionally may contain cargo-DNA and is normally not infectious upon mechanical inoculation of plant material, into whole plants of the Gramineae family or into viable parts thereof.

Contrary to all expectations, in the course of the investigations carried out within the scope of this invention it has surprisingly been shown that in using the method according to the invention it is now also possible for plants from the monocotyledon group, but especially from the family Gramineae, to become transformed in a specifically directed manner using certain transfer microorganisms such as, for example, *Agrobacterium tumefaciens*, that is to say, now also important representatives from the monocotyledon group, especially cultivated plants belonging to the Gramineae family, are accessible to infection by the said transfer microorganism.

The plants transformed in this manner can be identified by suitable methods of verification. There has proved especially suitable for this the use of virus genomes of plant-pathogenic viruses, such as, for example, Maize Streak Virus (MSV), by means of which successful transformations can be verified very efficiently by way of the disease symptoms that appear.

However, within the scope of the present invention it was now surprisingly found, that by applying a combination of suitable procedural measures, involving, for example, the use of a suitable plant material and a suitable inoculation site for the DNA probe to be introduced, it is possible to achieve that high a transformation frequency, that it would no longer be necessary to rely on disease symptoms in order to verify a positive transformation event. This would mean, however, that the Agrobacterium transformation system can now be applied directly to graminaceous monocots without any viral DNA being involved.

Attention is thus drawn especially to the broadening of the host spectrum of *Agrobacterium tumefaciens* to include Gramineae, by means of which even in representatives of this family a direct and specifically targeted manipulation of the genome is now possible.

In one of its aspects the present invention therefore relates to a process for inserting genetic material into monocotyledonous plants of the family Gramineae or viable parts thereof, wherein a transfer microorganism that contains the genetic material in a transportable form is made usable for infection of monocotyledons by employing suitable culturing and application methods that make possible the induction of the virulence gene functions of the transfer microorganism, and wherein monocotyledonous plants or viable parts thereof are infected therewith.

Further comprised by the invention are recombinant DNA, plasmid and vector molecules suitably adapted to the specific conditions of the process according to the invention and the transgenic plant products obtainable in accordance with the said process.

The present invention also relates to the use of vector systems such as those described above under c), and especially of novel vector systems such as, for example, bacteria of the strain *Agrobacterium tumefaciens* A136 (pTiBo542, pEAP18::Ca305) and *Agrobacterium tumefaciens* A136 (pTitBo542, pEA1)*Agrobacterium tumefaciens* (Rif$^R$) C58 (pTi C58; pEAP 200) and also *Agrobacterium tumefaciens* C58 (epTiC58; pEAP37), C58 (pTiC58; pEAP29), C58 (pTiC58; pEAP40) and also C58 (pTiC58, MSV 109) for the

DETAILED DESCRIPTION OF THE INVENTION

Figure 1:
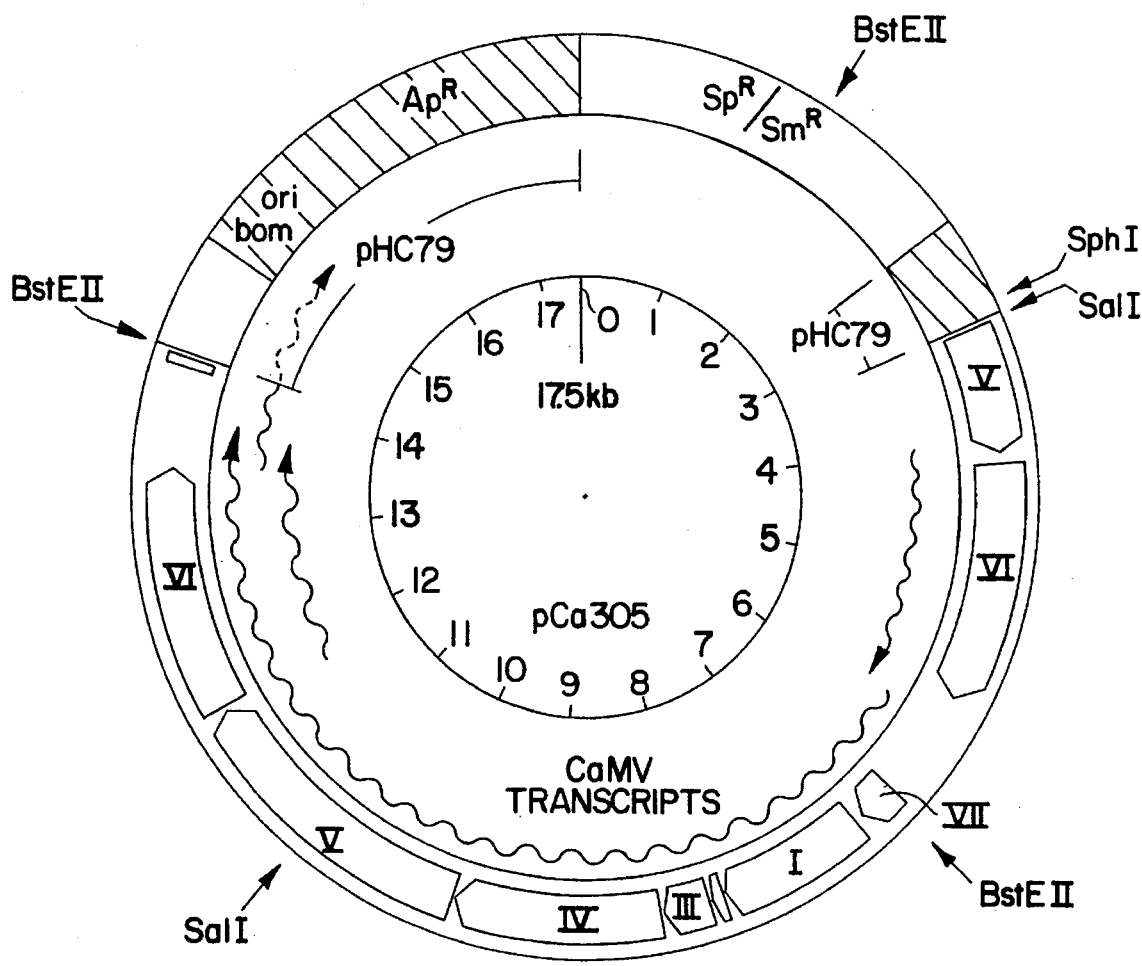
FIG. 1 is a map of plasmid pCa305. Ap$^R$ denotes ampicillin resistance; Sp$^R$/Sm$^R$ senotes spectinomycin/strepetomycin resistance; ori denotes origin of replication; bom denotes origin of mobilisation; BstEII, SphI and SalI each denote endonuclease restriction sites; I–VII denotes an open reading frame of cauliflower mosaic virus; and kb denotes kilobases.

To ensure a clear and uniform understanding of the description and the claims and also of the scope the said claims are to have, the following are given as definitions within the scope of the present invention.

Transfer-microorganism:
Microorganism that can transfer a part of its DNA into plant material (for example *Agrobacterium tumefaciens*).

T-replicon:
A replicon [Jacob F et al, 1963] that , with the aid of regulatory DNA sequences that are located on this replicon itself or on another replicon present in the same microorganism, can be transported entirely or partially into plant cells (example: the Ti-plasmid of *Agrobacterium tumefaciens*).

T-DNA-border sequences:
DNA sequences that, in one or more copies, effect DNA transfer into plant material with the aid of microbial functions.

Cargo-DNA:
A DNA of homologous or heterologous origin or a combination of homologous and heterologous DNA or a DNA prepared fully or partially by synthetic means, artificially inserted into a DNA vector.

Genomic DNA:
DNA derived from the genome of an organism.

c-DNA:
Copy of a mRNA produced by reverse transcriptase.

Synthetic DNA:
A DNA sequence that codes for a specific product or products or for a biological function and that is produced, fully or partially, by synthetic means.

Heterologous gene(s) or DNA:
A DNA sequence that codes for a specific product or products or for a biological function and that originates from a species different from that into which the said gene is to be inserted; the said DNA sequence is also referred to as a foreign gene or foreign DNA.

Homologous gene(s) or DNA:
A DNA Sequence that codes for a specific product or products or for a biological function and that originates from the same species as that into which the said gene is to be inserted.

Plant cell cultures:
Cultures of plant units such as, for example, protoplasts, cell culture cells, cells in plant tissues, pollen, pollen tubes, ovules, embryo sacs, zygotes and embryos in various stages of development.

Plants:

Any photosynthetically active member of the Planta kingdom that is characterised by a membrane-encapsulated nucleus, genetic material organised in the form of chromosomes, membrane-encapsulated cytoplasmatic organelles and the ability to carry out meiosis.

Plant cell:

Structural and physiological unit of the plant, consisting of a protoplast and a cell wall.

Protoplast:

"naked plant cell" without a cell wall isolated from plant cells or tissues, with the ability to regenerate to a cell clone or a whole plant.

Plant tissue:

A group of plant cells that are organised in the form of a structural and functional unit.

Plant organ:

A defined and clearly visible differentiated part of a plant such as, for example, a root, stem, leaf or embryo.

Fully transformed plants:

Plants in which the genome of each cell has been transformed in the desired manner.

tandemly duplicated form:

More than one vital DNA arranged in a head to head, a tail to tail or a head to tail orientation, which would the infectious vital DNA supposedly allow to become released based on an intramolecular recombination via transcription, reverse transcription or other methods of rearranging genetic material.

The present invention mainly relates to a method of introducing cloned viral DNA or functional equivalents thereof, that are normally not infectious upon mechanical inoculation of plant material, into plant material of plants that are naturally amenable, or, if not, are artificially made amenable, to transformation by a transfer microorganism such as, for example, a transfer microorganism of the genus Agrobacterium or viable parts thereof such as, for example, plant cell culture cells, which method comprises essentially the following procedural steps:

a) inserting cloned vital DNA or functional equivalents thereof, that preferably are capable of giving rise to a systemic infection, and which optionally may contain cargo DNA, into a T-replicon, for example a Ti-plasmid or Ri-plasmid of an Agrobacterium, in the vicinity of one or more T-DNA border sequences, the distance between said viral DNA and the T-DNA sequence or sequences being chosen such that vital DNA, including any cargo DNA present, is transferred m plant material;

b) introducing the replicon into a transfer microorganism, for example a microorganism of the genus Agrobacterium; and c) infecting plant material with the transfer microorganism that has been modified in accordance with b).

In a specific embodiment, the method according to the present invention essentially comprises the following partial steps:

a) isolating viral DNA or functional equivalents thereof (as described hereinafter), that preferably still have the potential for giving rise to a systemic infection upon incorporation into a plant or viable parts thereof, from infected plant material, and cloning said DNA in vectors of a suitable bacterium such as, for example, *Escherichia coli;* b) constructing a plasmid based on a T-replicon, for example a Ti-plasmid or Ri-plasmid of an Agrobacterium, preferably containing more than one vital genome or parts thereof that are in the vicinity of, but preferably between, one or more T-DNA border sequences, the distance between the vital DNA and the T-DNA border sequence or sequences being chosen such that said vital DNA, including any cargo DNA inserted thereinto, is transferred to plant material;

c) constructing a vector system by transferring the plasmid of step b) to a transfer microorganism (for example Agrobacterium tumefaciens or *Agrobacterium rhizogenes*);

$c_1$) optionally pretreating the so-transformed microorganism with plant exudate from dicotyledonous plants containing one or more compounds of the formula I, or with one or more compounds of the formula I in pure form;

d) growing the transfer microorganisms containing the T-replicon of step b) in a suitable culture medium known per se;

e) infecting plant material, but especially the meristematic regions of the said plant material, with the vector system constructed in accordance with c) and/or $c_1$), and thereby preferably releasing said vital DNA giving rise to a systemic infection.

Within the scope of the present invention there are to be understood by viral DNA and its functional equivalents especially the following types of DNA:

double stranded DNA forms of single-stranded DNA viruses (for example Gemini viruses, such as Maize Streak Virus (MSV)) and functional parts thereof;

cDNA copies of vital RNA or viroid RNA (for example of Tobacco-Mosaic virus or Cadang-Cadang viroid) and functional parts thereof;

any viable mutants of viruses and functional parts thereof;

portions of viral DNA that are still capable of giving rise to a systemic infection;

equivalents of the above-listed types of DNA in tandem form and equivalents of the above-listed types of DNA with incorporated Cargo-DNA.

It is possible to employ as the viral DNA that can be used within the scope of the process according to the invention, without this implying any limitation, for example DNA of Caulimo viruses, including Cauliflower Mosaic Virus (CaMV).

Representatives from the Canlimo viruses group, but especially Cauliflower Mosaic Viruses, are especially suitable for use within the scope of the process according to the invention, since owing to their genome structure (double-stranded DNA) they are directly accessible to genetic manipulation.

Besides, also representatives of the Gemini viruses, the genome of which is constructed from single-stranded (ss) DNA, can be suitably used within the scope of the present invention as vectors for transferring genetic material. This is, because the Gemini viruses form ds-DNA in the course of their development cycle and are thus accessible to direct genetic manipulation. To be mentioned here by way of exemplification are, for example, Bean Golden Mosaic Virus (BGMV), Chloris Striate Mosaic Virus (CSMV), Cassave Latent Virus (CLV), Curly Top Virus (CTV), Maize Streak Virus (MSV), Tomato Golden Mosaic Virus (TGMV) and Wheat Dwarf Virus (WDV).

Suitable transfer microorganisms that are capable of transferring genetic material to plants and can be used in the process according to the invention are especially microorganisms that contain a T-replicon.

There are to be understood by microorganisms that contain a T-replicon especially bacteria, preferably soil bacteria and, of these, especially those of the genus Agrobacterium.

Obviously, only strains of bacteria that are harmless, that is to say, for example strains of bacteria that are not viable in a natural environment or that do not cause any ecological problems, can be used within the scope of the process according to the invention.

A suitable T-replicon is especially a bacterial replicon, such as a replicon of Agrobacterium, especially a Ti- or Ri-plasmid of an Agrobacterium.

Ti-plasmids have two regions that are essential for the production of transformed cells. In dicotyledonous plants one of these, the transfer-DNA region, is transferred to the plant and leads to the induction of tumors. The other, the virulence-conferring (vir) region, is essential only for the development but not for the maintenance of the tumours. The transfer-DNA region can be increased in size by incorporating foreign DNA without its ability to be transferred being impaired. By removing the tumour-causing genes, as a result of which the transgenic plant cells remain non-tumorous, and by incorporating a selective marker, the modified Ti-plasmid can be used as a vector for the transfer of genetic material into a suitable plant cell.

The vir-region effects the transfer of the T-DNA region of Agrobacterium to the genome of the plant cell irrespective of whether the T-DNA region and the vir-region are present on the same vector or on different vectors within the same Agrobacterium cell. A vir-region on a chromosome likewise induces the transfer of the T-DNA from a vector into a plant cell.

Preferred is a system for transferring a T-DNA region from an Agrobacterium into plant cells which is characterised in that the vir-region and the T-DNA region lie on different vectors. Such a system is known as a "binary vector system" and the vector containing the T-DNA is called a "binary vector".

Any T-DNA-containing vector that is transferable into plant cells and that allows detection of transformed cells is suitable for use within the scope of this invention.

Preferred within the scope of the present invention is a T-replicon such as, for example, a Ti-plasmid or an Ri-plasmid of an Agrobacterium that contains, adjacent to one or more T-DNA border sequences, but preferably between the said border sequences, cloned viral DNA, for example DNA of Cauliflower Mosaic Virus (CaMV) or Maize-Streak Virus (MSV), which, of desired, may contain incorporated Cargo-DNA, the distance between vital DNA and the T-DNA border sequence(s) being chosen such that the vital DNA, including any Cargo-DNA that may be present, is transferred into plant material.

The viral DNA to be introduced into the plant cell is preferably represented by one or more vital replicons or parts of a vital replicon incorporated in a manner that allows release and replication of the viral replicon in the plant cell independently of the chromosomal DNA.

Especially preferred are constructions that contain more than one viral DNA in a tandemly duplicated form in a head to head, a tail to tail or a head to tail arrangement, which would the infectious vital DNA allow to become released based on an intramolecular recombination via transcription, reverse transcription or other methods of rearranging genetic material.

It is possible to use as Cargo-DNA either homologous or heterologous gene(s) or DNA as well as synthetic gene(s) or DNA in accordance with the definition given within the scope of the present invention.

The coding DNA sequence can be constructed exclusively from genomic DNA, from cDNA or from synthetic DNA. Another possibility is the construction of a hybrid DNA sequence consisting of both cDNA and genomic DNA and/or synthetic DNA.

In that case the cDNA may originate from the same gene as the genomic DNA, or alternatively both the cDNA and the genomic DNA may originate from different genes. In any case, however, both the genomic DNA and/or the cDNA may each be prepared individually from the same or from different genes.

If the DNA sequence contains portions of more than one gene, these genes may originate from one and the same organism, from several organisms that belong to more than one swain, one variety or one species of the same genus, or from organisms that belong to more than one genus of the same or of another taxonomic trait (kingdom).

The present invention relates also to the construction of cargo DNA comprising chimaeric recombinant DNA molecules that comprise an expressible DNA, but especially a structural gene, preferably a heterologous structural gene, in operable linkage with expression signals active in plant cells, such as promoter and termination sequences, as well as, optionally, with further coding and/or non-coding sequences of the 5' and/or 3' region.

There are suitable for use in the process according to the invention especially all those structural genes which upon expression lead to a protective effect in the transformed plant cells and also in the tissues developing therefrom and especially in the plants, for example increased resistance to pathogens (for example to phytopathogenic fungi, bacteria, viruses, etc.); resistance to chemicals [for example to herbicides (e.g. triazines, sulfonylureas, imidazolinones, triazole pyrimidin, bialaphos, glyphosate, etc.), insecticides or other biocides]; resistance to adverse environmental factors (for example to heat, cold, wind, adverse soil conditions, moisture, dryness, etc.).

Within the scope of this invention, special mention is to be made of structural genes that are associated with the control of plant pathogens and parasites.

Resistance to insects can be conferred, for example, by a gene coding for a polypeptide that is toxic to insects and/or their larvae, for example the crystalline protein of Bacillus thuringiensis [B.t.]. Especially preferred within the scope the present invention are synthetic B.t.

A second class of proteins mediating resistance to insects comprises the protease inhibitors. Protease inhibitors are a normal constituent of plant storage structures and are therefore normally located in vacuoles or protein bodies. It has been demonstrated that a Bowman-Birk protease inhibitor isolated from soybeans and purified inhibits the intestinal protease of Tenebrio larvae [Birk et al (1963)]. The gene that codes for the trypsin inhibitor from the cowpea is described in Hilder et al (1987).

A gene that codes for a protease inhibitor can, in a suitable vector, be brought under the control of a plant promoter, especially of a constitutive promoter, for example the CaMV 35S promoter. The gene, for example the coding sequence of the Bowman-Birk protease inhibitor from the soybean, can be obtained by the cDNA cloning method. A further possible method of producing a protease inhibitor is synthetic manufacture, provided that the protease inhibitor comprises fewer than 100 amino acids, for example the trypsin inhibitor of the lima bean. The coding sequence can be predicted by reverse translation of the amino acid sequence. In addition, them are incorporated at both ends restriction cleavage sites suitable for the vector desired in each particular case. The synthetic gene is produced by synthesis of overlapping oligonucleotide fragments of from 30 to 60 base pairs, by first subjecting those fragments to a kinase reaction, then linking them to one another [Maniatis et al (1982)] and finally cloning them in a suitable vector. By means of DNA sequencing it is then possible to identify a clone that has the insert in a correct orientation. For insertion into the protoplasts, isolated plasmid DNA can be used.

In this connection, mention should also be made of hydrolyric enzymes, which are capable of bringing about the breakdown of the cell walls of plant pathogens themselves, or at least assist that breakdown in conjunction with other substances in the sense of synergy.

The majority of insects, for example, have a cuticular skeleton in which chitin micelles in lamellar layers are embedded in a base substance. A great many phytopathogenic fungi also contain chitin as an integral part of their hypha and spore structures, for example Basidiomycetes (smut and rest fungi), Ascomycetes and Fungi imperfecti (including Alternaria and Bipolaris, *Exerophilum turcicum*, Colletotricum, Gleocercospora and Cercospora). Chitinase is capable of inhibiting the mycelial growth of certain pathogens in vitro. A plant organ or tissue that is capable of expressing chitinase constiutively or in response to the penetration of a pathogen could therefore protect itself from attack by a large number of different fungi.

A further gene, which encodes an enzyme which presumably plays a central role in the plant's defence mechanism against pathogens is the β-1,3-glucanase gene, that may thus also be used for protecting plants against a fungal attack, alone or im combination with a chitinase gene.

A further class of genes that may be used within the scope ot this invention are the so-called lyric peptides. These are natural or synthetic peptides having anti-pathogenic activity which are capable of penetrating, lysing or otherwise damaging the cell membrane of pathogens. Representatives of such lyric peptides that may be used within the scope of the present invention are known both from animal sources [including insects] and from plant and microbial sources and include, for example, the defensines, cercopines, thionines and mellitines of mammals, and the defensines, magainines, attacines, dipterines, sapecines, caerulines and xenopsines of insects, and hybrids thereof. The amino acid sequences of various lyric peptides are shown in the following publications: WO 89/11291; WO 86/04356; WO 88/05826; US 4,810,777; WO 89/04371.

Lyric peptides in the broadest sense of the term are also to be understood as being compounds whose ability to penetrate, lyse or damage cell membranes is based on enzymatic activity, for example lysozymes and phospholipases.

Moreover, reciprocal use of expression and exogenous application may also be envisaged, the lytic peptides especially being suitable for the latter purpose, in conjunction with the auxiliaries and/or additives customarily used for this purpose.

A further class of genes that may be used within the scope of the present invention comprises genes which encode pathogenesisrelated proteins [PRPs] such as PR-1A, PR-1B, PR-1C, PR-R major, PR-R minor, PR-P, PR-Q, PR-2, PR-2', PR-2", PR-N, PR-O, PR-)', PR-4, SAR8.2a-e, cucumber chitinase/lysozyme, cucumber basic peroxidase, tobacco basic glucanase and tobacco basic chitinase/lysozyme, tobacco acidic chitinase/lysozyme. Examples of the above genes and proteins including chimeric genetic constructs comprising the said genes are provided in EP-A 392,225 and in the co-pending U.S. patent application Ser. No. 848,506.

The DNA sequence according to the invention can also be used in ideal manner for the production of desirable and useful compounds in the plant cell as such or as part of a unit of higher organisation, for example a tissue, callus, organ, embryo or a whole plant.

Genes that may also be used within the scope of the present invention include, for example, those which lead to increased formation of reserve or stored substances in leaves, seeds, tubers, room, stems, etc. or in the protein bodies of seeds. The desirable substances that can be produced by transgenic plants include, for example, proteins, carbohydrates, amino acids, vitamins, alkaloids, flavins, perfumes, colourings, fats, etc..

There may also be associated with the DNA sequence according to the invention structural genes that code for pharmaceutically acceptable active substances, for example hormones, immunomodulators and other physiologically active substances.

The genes that can come into consideration within the scope of this invention therefore include, but are not limited to, for example, plant-specific genes, such as the zein gene from maize, the avenin gene from oats, the glutelin gene from rice, etc., mammal-specific genes, such as the insulin gene, the somatostafin gene, the interleukin genes, the t-PA gene, etc., or genes of microbial origin, such as the NPT II gene, etc. and synthetic genes, such as the insulin gene, etc..

Apart from naturally occurring structural genes that code for a useful and desirable property, within the scope of this invention it is also possible to use genes that have been modified previously in a specific manner using chemical or genetic engineering methods.

Furthermore, the broad concept of the present invention also includes genes that are produced entirely by chemical synthesis. Genes or DNA sequences that may be used within the scope of the present invention are therefore both homologous and heterologous gene(s) or DNA and also synthetic gene(s) or DNA according to the definition given within the scope of the present invention. The insulin gene may be mentioned at this point as an example of a synthetic gene.

In order to ensure the expression of the said structural genes in the plant cell, it is advantageous for the coding gene sequences first to be linked in operable manner to expression sequences capable of functioning in plant cells.

The hybrid gene constructions within the scope of the present invention therefore comprise, in addition to the DNA sequence according to the invention, one or more structural gene(s) and, in operable linkage therewith, expression signals which include both promoter and terminator sequences and other regulatory sequences of the 3' and 5' untranslated regions.

Any promoter and any terminator capable of bringing about an induction of the expression of a coding DNA sequence (structural gene) may be used as a constituent of the hybrid gene sequence. Especially suitable are expression signals originating from genes of plants or plant viruses. Examples of suitable promoters and terminators are those of the Cauliflower Mosaic Virus genes (CaMV) or homologous DNA sequences that still have the characteristic properties of the mentioned expression signals. Also suitable are bacterial expression signals, especially the expression signals of the nopaline synthase genes (nos) or the octopine synthase genes (ocs) from the Ti-plasmids of *Agrobacterium tumefaciens*.

Within the scope of this invention, preference is given to the 35S and 19S expression signals of the CaMV genome or their homologues which can be isolated from the said genome using molecular biological methods, as described, for example, in Maniatis et al (1982), and linked to the coding DNA sequence.

Within the scope of this invention, homologues of the 35S and 19S expression signals are to be understood as being sequences that, despite slight sequence differences, are substantially homologous to the starting sequences and still fulfil the same function as those starting sequences.

In accordance with the invention there may be used as starting material for the 35S transcription control sequences, for example, the SeaI fragment of the CaMV strain "S", which includes the nucleotides 6808–7632 of the gene map [Frank G et al (1980)].

The 19S promoter and 5' untranslated region is located on a genome fragment between the PstI site (position 5386) and the HindIII site (position 5850) of the CaMV gene map [Hohn et al (1982)]. The corresponding terminator and 3' untranslated region is located on an EcoRV/BglII fragment between positions 7342 and 7643 of the CaMV genome.

Also preferred within the scope of this invention are the expression signals of the CaMV strain CM 1841, the complete nucleotide sequence of which is described in Gardner RC et al (1981).

A further effective representative of a plant promoter that may be used is an over-producing plant promoter. Provided that this type of promoter is operably linked to the gene sequence that codes for a desired gene product, it should be capable of mediating the expression of the said gene sequence.

Over-producing plant promoters that may be used within the scope of the present invention include the promoter of the small subunit (ss) of ribulose-1,5-biphosphate carboxylase from soybeans and also the promoter of the chlorophyll-a/b-binding protein. These two promoters are known for the fact that they are induced by fight in eukaryotic plant cells [see, for example, Genetic Engineering of Plants, An Agricultural Perspective, Cashmore A (1983)].

Further promoters useful in the present invention to express an associated structural gene are promoters whose expression are known to vary in a tissue specific manner such as, for example, the promoter of the maize phosphoenol pyruvate carboxylase (PEPC; Hudspeth, R. L. and Grula, J. W., Plant Molecular Biology 12:579–589, 1989). Also to be mentioned here by way of exemplification is a maize pith preferred promoter, or a pollen specific promoter.

A developmentally regulated promoter can also be used. Of course, in the present invention, any promoter which is functional in the desired host plant can be used to direct the expression of an associated gene.

It is often advantageous to incorporate a leader sequence between the promoter sequence and the adjacent coding DNA sequence, the length of the leader sequence being so selected that the distance between the promoter and the DNA sequence according to the invention is the optimum distance for expression of the associated structural gene.

Further regulatory DNA sequences that may be used for the construction of chimeric genes include, for example, sequences that are capable of regulating the transcription of an associated DNA sequence in plant tissues in the sense of induction or repression.

There are, for example, certain plant genes that are known to be induced by various internal and external factors, such as plant hormones, heat shock, chemicals, pathogens, oxygen deficiency, light, stress, etc..

As an example of gene regulation by a plant hormone, mention should here be made of abscisic acid (ABS), which is known to induce the excess of mRNAs which occurs during the late embryonal phase in cotton. A further example is gibberellic acid (GA3) which induces malate synthase transcripts in castor beans and isoenzymes of a-amylase in the aleurone layers of barley.

The activity of glucanase and chitinase in bean leaves can be markedly increased by treatment with the stress hormone ethylene. In the case of chitinase, this induction effect is controlled via the promoter of the chitinase gene, and it was possible to demonstrate this by reporter gene tests using a promoter from the chitinase gene of beans (*Phaseolus vulgaris*).

The regulation of heat-shock-sensitive protein genes of soybeans has been studied in detail. Treating the plants for several hours at a temperature of 40° C. results in the de novo synthesis of so-called heat-shock proteins. A large number of those genes have since been isolated, and their regulation has been analysed in detail. The expression of those genes is controlled primarily at the transcription level. For example, if the promoter of the hps70 gene is fused with the neomycin phosphotransferase II (NPT II) gene, the chimeric gene so formed can be induced by a heat shock [Spena et al, 1985].

Another class of genes that are inducible in plants comprises the light-regulated genes, especially the nuclear-coded gene of the small subunit of ribulose-1,5-biphosphate carboxylase (RUBISCO). Morelli et al (1985) have shown that the 5'-flanking sequence of a RUBISCO gene from the pea is capable of transferring light-inducibility to a reporter gene, provided the latter is linked in chimeric form to that sequence. It has also been possible to extend this observation to other light-induced genes, for example the chlorophyll-a/b-binding protein.

The alcohol dehydrogenase genes (adh genes) of maize have been the subject of intensive research. The adh1-s gene from maize was isolated, and it was shown that a part of the 5'-flanking DNA is capable of inducing the expression of a chimeric reporter gene (e.g. chloramphenicol acetyl transferase; CAT) when the temporarily transformed tissue was subjected to anaerobic conditions [Howard et al (1987)].

A further group of regulable DNA sequences comprises chemically regularable sequences that are present, for example, in the PR (pathogenesis-related) protein genes of tobacco and are inducible by means of chemical regulators such as those described in EP-A 332,104.

The regulatable DNA sequences mentioned by way of example above may be of both natural and synthetic origin, or they may comprise a mixture of natural and synthetic DNA sequences.

It is often advantageous for the expressible DNA, but especially the structural gene that is to be inserted, to comprise a sequence that codes for an N- or a C-terminal signal peptide capable of functioning in the plant cell, or to be linked in the 5'- or 3'-terminal region to such a sequence.

That N-terminal signal peptide is a transport signal that is found at the N-terminal end of proteins transported via the endomembrane system. This signal sequence ensures that the said proteins first pass into the endoplasmic reticulum, where the signal peptide is split off proteolytically from the precursor protein as soon as it has fulfilled its function. By virtue of its specific function, this type of signal peptide sequence has been conserved to a high degree during evolution in all living cells, irrespective of whether they are bacteria, yeasts, fungi, animals or plants.

At the C-terminal end of vacuolar proteins, on the other side, sequences may be found that are involved in directing the expression of the associated coding part to the plant vacuole. Examples of these so-called 'vacuolar targeting' sequences are provided, for example, in EP-A 462,065

Moreover, the DNA molecule may comprise further sections of sequence that code for peptide fragments which as a whole contribute towards improving the competence for admission into the vacuole, for example the propeptide fragment discovered by Matsuoka K and Nakamura K in the N-terminal extension of sporamine [Matsuoka K and Nakamura K (1991)].

The present invention therefore also includes chimeric genetic constructions that comprise in operable linkage with a structural gene or any other expressible DNA sequences, further regulatory sections of DNA sequence permitting, for example, specifically controlled induction or repression of gene expression.

The different sections of DNA sequence comprising a T-replicon and one or more viral DNAs, which optionally may contain Cargo-DNA comprising one of the chimeric constructs described hereinbefore, can be linked to one another to form a functional unit by methods known per se. Suitable methods include, for example, the in vivo recombination of DNA sequences that have homologous sections and the in vitro linking of restriction fragments.

In the above in vivo and/or in vitro processes for assembling the different sections of the said functional unit, cloning vectors may be involved such as, for example plasmid or virus (bacteriophage) vectors having replication and control sequences originating from species that are compatible with specific host cells.

The cloning vector generally carries an origin of replication, especially an origin of replication that is capable of functioning in E. coli, in Agrobacterium or in both, and, in addition, specific genes that lead to phenotypic selection features in the transformed host cell, especially to resistance to antibiotics or to specific herbicides. The transformed vectors can be selected on the basis of those phenotypic markers after transformation in a host cell.

Especially suitable within the scope of the present invention are so-called shuffle vectors, which can stably replicate not only in one but in at least two different host organisms such as, for example, in *E. coli* and in *Agrobacterium tumefaciens*, in the presence of a suitable selection marker.

Selectable phenotypic markers that may be used within the scope of this invention include, for example, resistance to ampicillin, tetracycline, hygromycin, kanamycin, methotrexate, G418 and neomycin, but this list, which is given by way of example, is not intended to limit the subject of the invention.

Suitable host cells within the scope of this invention are prokaryotes, including bacterial hosts, for example *A. tumefaciens, E. coli, S. typhimurium* and *Serratia marcescens*, and also cyanobacteria. Eukaryotic hosts, such as yeasts, mycelium-forming fungi and plant cells, may also be used within the scope of this invention.

The splicing of the hybrid gene construction according to the invention into a suitable cloning vector is carried out using standard methods, such as those described, for example, in Maniatis et al (1982).

As a role, the vector and the DNA sequence to be spliced in are first cleaved with suitable restriction enzymes. Suitable restriction enzymes are, for example, those that yield fragments having blunt ends, for example SmaI, HpaI and EcoRV, or enzymes that form cohesive ends, for example EcoRI, SacI and BamHI.

Both fragments having blunt ends and those having cohesive ends that are complementary to one another can be linked again using suitable DNA ligases to form a continuous uniform DNA molecule.

Blunt ends can also be produced by treatment of DNA fragments that have projecting cohesive ends with the Klenow fragment of the *E. coli* DNA polymerase to fill up the gaps with the corresponding complementary nucleotides.

On the other hand, cohesive ends can also be produced by artificial means, for example by the addition of complementary homopolymeric tails to the ends of a desired DNA sequence and of the cleaved vector molecule using a terminal deoxynucleotidyl transferase, or by the addition of synthetic oligonucleotide sequences (linkers) that carry a restriction cleavage site, and subsequent cleavage with the appropriate enzyme.

The above assembling procedure may preferably result in a recombinant DNA molecule comprising a T-replicon such as, for example, a Ti-plasmid or an Ri-plasmid of an Agrobacterium that contains, adjacent to one or more T-DNA border sequences, but preferably between the said border sequences, one or more viral DNAs, for example DNA of Cauliflower Mosaic Virus (CaMV) or Maize-Streak Virus (MSV), which, if desired, may contain incorporated Cargo-DNA preferably comprising one of the chimeric constructs outlined hereinbefore, the distance between viral DNA and the T-DNA border sequence(s) being chosen such that the vital DNA, including any Cargo-DNA that may be present, is transferred into plant material.

The recombinant DNA according to the invention can than be introduced into a transfer microoganism, but preferable into a transfer microprganism of the genus Agrobacterium, using one of the methods well known in the art. The transfer is preferably carried out by "triparental mating", as described in detail in Rogers SG et al (1986) and in the following examples.

The thus obtained transfer microorganisms are then grown in a culture medium and under conditions known per se.

In a specific embodiment of the present invention, the transfer microorganisms such as, for example, *Agrobacterium tumefaciens*, are advantageously gown in one of the nutrient media normally used for culturing microorganisms at a temperature of from 15° C. to 40° C. over a period of from 30 to 60 hours (h) in a stirred liquid culture. The preferred growing temperature is from 24° C. to 29° C. Them then follow one or more sub-culturing steps, preferably in the same medium, advantageously in a dilution ration of 1:20, each of which lasts for a period of from 15 to 30 h, preferably from 18 to 20 h. In these cases, too, the culture temperature is from 15° C. to 40° C., preferably from 24° C. to 29° C.

If thermophilic microorganisms are used, the growing temperature may be distinctly higher than 40° C.

Obviously, it is also possible for other culturing measures suitable for growing the transfer microorganisms to be carried out within the scope of this invention.

For example, it is also possible to use solid culture media, for example, can be produced using agarose or alginate or any other suitable solidifying agent.

The thus pretreated transfer microorganisms can then be used for transforming plant material, whereby the recombinant DNA according to the invention becomes transferred into the cells of the said plant material.

DNA transfer to plants can be effected by one of the known systems, for example by the binary vector system described by An, G. et al, 1985. This vector system can be improved by inserting e.g. sequences for a homologous recombination of the DNA to be transferred to the plant.

Suitable plant material comprises both whole plants as well as parts of plants. Parts of plants are for example also protoplasts, cell culture cells, cells in plant tissue, pollen, pollen robes, egg-cells, embryo-sacs, zygotes or embryos in different stages of development as well as whole plants.

Within the scope of the present invention, it has surprisingly been possible to show that the frequency of transformation of the inoculated plants depends not only to a decisive degree on the application site on the plant, but also very especially on the stage of development of the particular plant being tested, as well as on other parameters.

An important part of the present invention therefore relates to a more sophisticated differentiation of the application site on the plant and thus to the specifically directed application of the transforming microorganism-containing inoculation solution at precisely defined sites on the plant, resulting in a significant increase in the frequency of transformation of the inoculated plants. Furthermore, the frequency of transformation can be even further increased by suitable selection of the time of application as regards the stage of development of the recipient plant.

These observations have led to the surprising finding that by applying a combination of suitable procedural measures, involving, for example, the use of a suitable plant material and a suitable inoculation site for the DNA probe to be introduced, it is possible to achieve that high a transformation frequencies, that would be no longer necessary to further rely on disease symptoms in order to verify a positive transformation event. This would mean, however, that the Agrobacterium transformation system can now be applied directly to graminaeeous monocots without any vital DNA being involved.

The present invention thus also relates especially to a novel process for inserting genetic material into plants, but especially into monocotyledenous plants, or viable parts thereof, which is characterised in that transfer microorganisms that are capable of inserting the said genetic material into monocotyledenous plants or viable parts thereof and that contain the genetic material to be inserted in a transportable form, are inoculated in the form of a microorganism suspension into a mefistematic tissue region of the plants or of a viable part thereof.

In particular, the present invention relates to an improved process for transforming monocotyledonous plants using strains of Agrobacterium that are capable of carrying out the said transformation, which process is characterised in that the time of inoculation as regards the stage of development of the recipient plant, and the site of inoculation in the region of the growth zones, are so coordinated that there is a significant increase in the rates of transformation that can be achieved by comparison with known processes.

The target plants to be infected with an Agrobacterium transfer microorganism according to the invention are preferable those plants or viable parts thereof, that are in a state of competence for an Agrobacterium infection. This state of competence may be found during all developmental stages of the recipient plant extending over a priod that commences with the development of the plant embryo and ends with the flowering stage, and thus with the growth and development (differentiation) phase of the recipient plant.

Considering this a spect plants that have reached the stage of development extending between seed germination and the 4-leaf stage have proved to be especially suitable for the application of the process according to the invention.

Preferred are 1- to 3-day-old seedlings in which the distance between the scutellar node and the apical coleoptile tip is from 1 to 2 cm. Plants that are at a stage of development that renders possible a clear identification of the coleoptilar node are, however, especially suitable.

Especially preferred are seedlings which are germinated from immature embryos. The tissue of mature embryo-germinated seedlings is soft, indicating a less rigid cell wall. This may physically or physiologically favour Agrobacterium mediated T-DNA transfer. Most preferred are seedlings having developed the fith and sixth leaf primordia.

In a further embodiment of the present invention, the inoculation of the microorganism-containing transforming inoculation solution is carried out on the immature developing embryo after pollination and fertilisation of the ovules by the sperm nucleus, but preferably before the seed coat has developed. Immature embryos are either inoculated immediately after isolation or are first germinated up to 3 days in the dark before being involved into the inoculation procedure.

When using very early, non-germinated, immature embryos those morphological stages are preferred that already show signs of differentiation. Especially preferred are immature embryos that have developed at least the first leaf initials as well as later stages.

To prepare the inoculation solution, the cells are preferably centrifuged off and resuspended in a concentration, suitable for infection, in a suitable inoculation medium, for example in $1/20$ th part volume of an MSSP medium [Stachel et al, 1985]. The infection process is commenced in accordance with the invention by bringing the afore-described transfer microorganism into contact with the plant material, for example by incubation with protoplasts, by wounding whole plants or portions of tissue or, especially, by injection of the microorganism suspension directly into the plant.

The introduction of the transforming microorganism-containing inoculation solution into the plant can be carried out by a wide variety of methods, for example by artificially wounding the epidermal tissue and rubbing the microorganism-containing transforming suspension into the wounded tissue, by incubating [co-cultivating] the transfer microorganism together with the wounded plant tissue or, alternatively, a plant protoplast, or by injecting the transforming suspension into the plant material to be transformed.

Injection of the inoculation solution using a hypodermic syringe is preferred, by means of which a very accurately located and thus specifically directed application at precisely defined sites on the plant can be effected.

As a rule, hypodermic syringes with exchangeable needles having a cross-section of from 0.1 to 0.5 mm are used, adapted to the requirements and special demands of the plant species concerned and to its stage of development at the time of application. The volume applied also varies as a function of the plant species concerned and its stage of development and ranges from 1 to 20 µl, an application volume of from 5 to 10 µl being preferred.

Obviously, it is also possible to use other suitable aids for the targeted application of the inoculation solution into the plant, such as, for example, very fineyl drawn glass capillaries, by means of which, using micromanipulators, the smallest application quantities can be applied into accurately defined tissue regions of the plant (such as, for example, the meristem). This approach would be especially suitable of immature plant embryos are involved owing to the limited size of these objects. In this case the preferred application volume is in a range of from 0.5 µl to 5 µl but especially from 2 µl to 4 µl.

The inoculation of the microorganism-containing transforming suspension is carried out preferably in regions of the plant or viable parts thereof that contain mefistematic tissue. These are portions of tissue that are active as regards division and metabolism and that contain, especially, omnipotent embryonic cells from which are thus ultimately also the starting point for the development of the germ cells.

A repeated application of the transforming microorganism-containing inoculation solution into the meristematic tissue regions of the plant is especially preferred within the scope of this invention.

A particularly suitable application site for the insertion of the transforming microorganism-containing suspension into plantlets already differentiated into stem, root and leaves in the boundary area between root and stem, the so-called root collar.

In a special embodiment of the present invention, the application of the transforming microorganism-containing suspension is effected on the seedling approximately from 1 to 3 days after germination. Preferred application sites are the coleoptile and coleorhiza areas.

Very good transformation results can be achieved by application in the immediate vicinity of, or especially by application directly into, the coleoptilar node.

Accordingly, a further especially preferred embodiment of the present invention is characterised in that the application of the transforming microorganism-containing inoculation solution is carried out from 1 to 3 days after germination in the immediate vicinity of, or directly into, the coleoptilar node of the seedling.

In a further specific embodiment of the present invention, the application of the transforming microorganism-containing solution is carried out directly into the coleoptilar node tissue after decapitating the tip of the coleoptile in the region of the coleoptilar node. The majority of the plumule can be removed without the further development of the seedling being adversely affected.

A preferred method of application in this case, too, includes the use of hypodermic syringes, it being possible for the depth of puncture to be varied within specific limits as a function of the removal of the decapitated region of the coleoptilar node. However, inoculation directly into the coleoptilar node tissue is in any case preferred. Application of the inoculation solution can be effected either in the peripheral tissue areas or, especially, in the central part of the exposed coleoptilar node tissue, the areas of meristemafic tissue being especially preferred.

In using immature embryos, apart from the inoculation techniques already mentioned it is also possible to use a process in which the embryo is first of all, in preparation, removed from the mother plant and then brought into contact with the transfer microorganism in a suitable culture medium [IK Vasil, 1984; Pareddy D et al, 1987).

A further preferred method of application includes co-cultivating of shoots of plant seedlings germinated from immature embryos. with the Agrobacterium containing solution, said shoots being obtainable by germinating embryos on a suitable agar medium and isolating the developing shoots from the seedlings by cutting just below the coleoptilar node, where the shoot meristem is located. In particular, the shoots are dipped into the Agrobacterium suspension and then preferably subjected to vacuum infiltration. The infilitrated shoots are cultured on the agar plates of a suitable medium, but preferably a MS medium.

The procedure for applying the inoculation solution to the plant or seedling may likewise vary, but can easily be optimised for different species of plant. These optimising tests can be carried out, without appreciable expenditure by any person skilled in the art, within the limits of a standard optimising programme in accordance with the guidelines of the present invention.

In addition m the parameters already mentioned, the concentration and the growth phase of the inoculated transfer microorganisms are also of significance as regards the efficiency of the transformation. The preferred concentration ranges from $10^5$ to $10^{10}$ organism per ml of inoculation solution. An inoculation concentration of from $10^7$ to $10^9$ organisms/ml is especially preferred.

Dilution experiments carried out within the scope of this invention have shown that as dilution of the inoculation solution increases the frequency of transformation decreases. The efficiency of the Agrobacterium-imparted DNA transfer m monocotyledonous plants is of the same order as the DNA transfer to dicotyledonous host plants (Results section, Point D).

Possible variations within the scope of the process according to the invention consequently reside in, for example, the choice of application method, the depth of puncture into the plant tissue, the composition and concentration of the bacterial suspension, and the number of inoculations carried out per infection.

A further measure that has proved to enhance the transformation frequency is extra-wounding of the plant tissue to be inoculated. This is especially relevant in those case where the co-cultivation approach is used such as, for example, if shoots of plant seedlings germinated from immature embryos are co-cultivated with an Agrobacterium-containing solution.

The transfer of genetic material to monocotyledonous plants or to viable parts thereof in accordance with the invention can also be carried out after pretreating the transfer microorganisms with a specific inducing agent consisting of an exudate of dicotyledonous plants or with certain compounds that can be isolated from this plant exudate. Obviously, it is also possible to use synthetically prepared or modified substances.

These inducing agents are especially compounds of the formula I

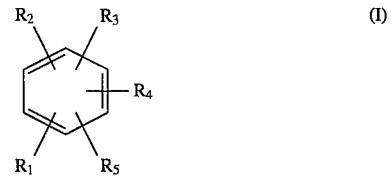

in which $R_1$, $R_2$, $R_3$, $R_4$ and $R_5$, independently of one another, each represents hydrogen or a substituent selected from the group comprising OH, COOH, CHO, COCH$_3$, OCH$_3$ and CH=CHCOOH, with the proviso that a minimum of one and a maximum of three of the radicals $R_1$ to $R_5$ represent hydrogen. These agents can be used individually or together.

Preferred within the scope of the invention are compounds of the following formula Ia

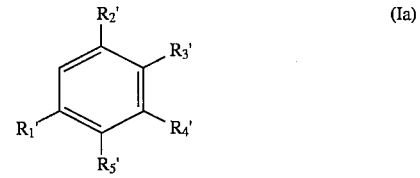

in which $R_1'$ and $R_4'$, independently of one another, each represents H, OH or OCH$_3$;

$R_2'$ represents H, COOH, CHO, COCH$_3$ or CH=CHCOOH; and $R_3'$ and $R_5'$, independently of one another, each represents H or OH, with the proviso that a minimum of one and a maximum of three of the radicals $R_1'$, $R_2'$, $R_3'$, $R_4'$ and $R_5'$ represent hydrogen.

Examples of compounds of the formula I and Ia are, inter alia:

4-hydroxy-3,5-dimethoxyacetophenone,
4-hydroxy-3-methoxyacetophenone,
4-hydroxy-3,5-dimethoxybenzaldehyde,
4-hydroxy-3-methoxybenzaldehyde
4-hydroxy-3,5-dimethoxybenzoic acid,
3,4,5-trihydroxybenzoic acid,
3,4-dihydroxybenzoic acid,
2,4-dihydroxybenzoic acid,
β-hydroxybenzoic acid,
1,2,3-trihydroxybenzene and
1,2-dihydroxybenzene and
2-(3,5-dimethoxy-4-hydroxyphenyl)acrylic acid;

this list is not of a limiting nature.

The specifically mentioned representatives of compounds of the formula I and Ia have been verified as natural constituents in plant exudates of dicotyledonous plants and are known as inducers of the virulence (vir-)gene functions of the *Agrobacterium tumefaciens* Ti-plasmid.

In many cases it is advantageous if the inducer is added to the culture medium from outside and thus sets the induction process in motion.

Plant cells or plants that have been transformed in accordance with the present invention can be selected by means of a suitable phenotypic marker. Examples of such phenotypic markers, which are not, however, to be construed as limiting, include antibiotic-resistance markers such as, for example, kanamycin-resistance genes and hygromycin-resistance genes, or herbicide-resistance markers such as, for example, the glyphosate resitance gene. Other phenotypic markers are known to the person skilled in the art and can likewise be used within the scope of this invention such as, for example, the β-glucuronidase [GUS] gene.

Especially preferred within this invention is a GUS gene, that is embedded in a sequence of eukaryotic origin, which has been shown to have a enhancing influence on the post-transcriptional expression efficiency in plant cells.

By using the process according to the invention it is possible to obtain not only transgenic plants with transformed somatic cells, but also especially plants that contain transformed germ cells from which, in the course of further cell and tissue differentiation, transformed ovules and/or pollen can develop.

After fertilisation with participation of transformed ovules and/or transformed pollen, seeds are obtained that contain transgenic embryos and that can be used to produce transgenic plants.

The method of this invention is suitable for infecting all plants with virus. Of the systematic units Gymnosperm and Angiospermat (including ornamentals), the latter are preferred.

Among the Angiospermae, plants of particular interest are, in addition to deciduous trees and shrubs, plants of the following families: Solanaceae, Cruciferae, Malvaceae, Compositae, Liliaceae, Vitaceae, Chenopodiaceae, Rutaceae, Cucurbitaceae, Bromeliaceae, Rubiaceae, Theaceae, Musaceae or Gramineae and of the order Leguminosae, in particular of the family Papilionaceae. Preferred plants are representatives of the Solanaceae, Cruciferae and Gramineae families.

The high yield cultivated plants such as maize, rice, wheat, barley, rye, oats or millet are to be singled out for special mention.

Target crops are for example those of plants of the genera Solanum, Nicotiana, Gossypium (cotton), Brassica (rape), Beta, Pisum, Phaseolus, Glycine, Helianthus, Allium, Triticum (wheat), Hordeum (barley), Avena (oats), Setaria, Sorghum (millet), Oryza (rice), Zea (maize), Cydonia, Pyrus, Malus, Rubus, Fragaria, Prunus, Aractis, Secale, Panicum, Saccharum, Coffea, Camellia, Musa, Ananas, Vitis, Citrus and Persea (avocado).

Of particular commercial importance is the range of hosts of Maize Streak Virus, which includes numerous monocotyledonous cultivated plants and cereals such as, for example, maize, rice, wheat, millet, sorghum and various African grasses.

The process according to the invention is especially suitable for infecting whole plants from the class of Monocotyledoneat or viable parts of those plants, such as, for example, plant tissue cultures or cell culture cells, with vital DNA and equivalents thereof. This invention therefore also relates to the transformed protoplasts, plant cells, cell clones, cell aggregates, plants and seeds and progeny thereof resulting from the process according to the invention, that have the novel property resulting from the transformation, and also to all hybridisation and fusion products of the transformed plant material that have the novel properties produced by the transformation.

The present invention also relates to transformed whole plants and viable parts of those plants, especially pollen, ovules, zygotes, embryos or any other reproductive material emerging from transformed germ-line cells.

The present invention furthermore includes also completely transformed plants that have been regenerated from viable parts of transformed monocotyledonous plants.

Monocotyledonous plants that are suitable for the use according to the invention include, for example, species from the following families: Alliaceat, Amaryllidaceae, Asparagaceae, Bromeliaceae, Gramineat, Liliaceat, Musaceae, Orchidaceae or Palmae.

Especially preferred are representatives from the Gramineae family, such as, for example, plants that are grown over a large area and produce high yields. The following may be mentioned as examples: maize, rice, wheat, barley, rye, oats and millet.

Other target crops for the application of the process according to the invention are, for example, plants of the following genera: Aliium, Avena, Hordeum, Oryzae, Panicum, Saccharin, Secale, Setaria, Sorghum, Triticum, Zea, Musa, Cocos, Phoenix and Elaeis.

A further object of the present invention thus relates to transgenic plants, but preferably to transgenic monocotyledonous plants, more preferably to transgenic monocotyledonous plants of the Gramineat family and most preferably to transgenic maize plants obtainable by a process according to the invention including the transgenic progeny of those transgenic plants.

It is thus a further object of the present invention to provide transgenic monocotyledonous plants of the Gramineae family, but preferably a transgenic maize plant, which are obtainable by a method according to the invention and the progeny thereof including propagules and seeds, comprising in an expressible form a chimeric DNA construct comprising an expressible DNA in operable linkage with expression signals active in plant cells of graminaeeous monocots, such as promoter and termination sequences, as well as, optionally, further coding and/or non-coding sequences of the 5' and/or 3' region.

Successful transformation by transferring T-DNA to the test plant concerned can be verified in a manner known per se, for example in the light of diesease symptoms [if viral DNA is involved in the transformation process], and also be molecular biological investigation including, especially, the "Southern blot" analysis.

The extracted DNA is first of all treated with restriction enzymes, then subjected to electrophoresis in 1% agarose gel, transferred to a nitrocellulose membrane [Southern, (1975)] and hybridised (DNA-specific activities of from $5\times10^8$ to $10\times10^8$ c.p.m./µg) with the DNA to be detected, which has previously been subjected to a nick-translation [Rigby et al,]. The filters are washed three times for one hour each time with an aqueous solution of 0.03M sodium citrate and 0.3M sodium chloride at 65° C. The hybridised DNA is made visible by blackening an X-ray film for from 24 to 48 hours.

The use of the method of this invention employing the above described vector system affords numerous advantages compared with the methods employed hitherto, viz.:

broadening the host range of an normally dicotyledon-specific transfer microorganism such as, for example, *Agrobacterium tumefaciens* or *Agrobacterium rhizomes* to monocotyledons;

inducing infectivity in viruses which it has so far not been possible to make infectious by artificial means (for example maize streak virus), by-passing natural vectors such as insects;

the possibility of manipulating viral DNA in a bacterial system such as *E. coli;* increasing the host range of viruses;

simplifying inoculation by avoiding DNA purification and very substantially reducing the amount of inoculum required for inoculation;

systemically infecting a whole plant by using vital DNA or equivalents thereof;

under control of bacterially coded functions, the T-DNA, including the selected vital DNA, can become integrated into the host genome. As regeneration of whole plants from single plant cells after transformation with bacteria is possible, vital DNA can be introduced into the nuclear genome of every cell in a plant. Such integrated virus genomes can then be transmitted sexually to offspring;

can prevent infection by other viruses;

can be a possible source of further copies of virus containing selected cargo DNA and which escape from the integrated copy via transcription, reverse transcription, homologous recombination or other methods of modifying genetic material.

In addition, superinfection of plants containing parts of viral genomes integrated into the nuclear DNA may a) permit the development of better viral vectors, as the expression of viral genes from nuclear DNA could make it possible to replace viral DNA with foreign DNA in the super-infecting virus; and b) contribute to a better understanding of host-parasite relationships and thus to substantially better protection of plants.

By means of the method of this invention, cargo DNA inserted into the virus genome can also be transported into plant material in which it proliferates. The proliferation in plants of the virus, and thus also of the foreign gene transported by it, is especially advantageous whenever it is desired to propagate plants asexually or to protect them direct and in the shortest possible time against harmful influences (for example by inserting a gene into the plants to impart resistance).

The method of this invention is in particular admirably suitable for insinuating selected genes into plant material, for example adult plants, in which they then proliferate.

The method of this invention can also be utilised in the field of plant protection for "immunising" plants against virus attack by means of a transfer micro-organism as described above by transforming plants with a weakened non-pathogenic or only slightly pathogenic virus, which has the result of protecting the plants from undesired further virus infections.

A further approach that may be used in the immunization process is introducing and expressing viral coat protein genes, which have proved to achieve a protective action, which protects the plant from infection with the corresponding virus. The expression of other virus genes such as, for example, satellite RNA also can result in a protective action against further vital infections.

It is thus a further object of the invention to provide a method of immunizing plants against an undesired virus attack, wherein a DNA exhibiting a protective action against further vital infections is introduced into the said plant to be protected by a method according to the invention.

The following Example, in which CaMV and MSV, respectively, are used as viruses, *E. coli* as cloning bacterium and *Agrobacterium tumefaciens* as vehicle bacterium, illustrates in more detail the construction and use of a suitable vector system. This Example can also be performed in similar manner with *Agrobacterium rhizomes*.

(A) NON-LIMITING EXAMPLES

General recombinant DNA techniques

Since many of the recombinant DNA techniques employed in this invention are a matter of routine for the person skilled in the art, it is better to give a short description of these generally used techniques here rather than to describe them every time they occur. Except where them is a specific indication to the contrary, all these procedures are described in the Maniatis et al (1982) reference.

A. Cleaving with restriction endonucleases

A reaction batch typically contains about 50 to 500 µg/ml of DNA in the buffer solution recommended by the manufacturer, New England Biolabs, Beverly, Mass. 2 to 5 units of restriction endonucleases are added for each µg of DNA and the reaction batch is incubated for from one to three hours at the temperature recommended by the manufacturer. The reaction is terminated by heating at 65° C. for 10 minutes or by extraction with phenol, followed by precipitation of the DNA with ethanol. This technique is also described on pages 104 to 106 of the Maniatis et al (1982) reference.

B. Treatment of DNA with polymerase in order to produce blunt ends 50 to 500 µg./ml of DNA fragments are added to a reaction batch in the buffer recommended by the manufacturer, New England Biolabs. The reaction batch contains all four deoxynucleotide triphosphates in concentrations of 0.2 mM. The reaction takes place over a period of 30 minutes at 15° C. and is then terminated by heating at 65° C. for 10 minutes. For fragments obtained by cleaving with restriction endonucleases that produce 5'-projecting ends, such as EcoRI and BamHI, the large fragment, or Klenow fragment, of DNA polymerase is used. For fragments obtained by means of endonucleases that produce 3'-projecting ends, such as PstI and SacI, the T4 DNA polymerase is used. The use of these two enzymes is described on pages 113 to 121 of the Maniatis et al (1982) reference.

C. Agarose gel electrophoresis and purification of DNA fragments from gels

Agarose gel electrophoresis is carried out in a horizontal apparatus, as described on pages 150 to 163 of the Maniafis et al reference. The buffer used is the tris-borate buffer described therein. The DNA fragments are stained using 0.5 µg/ml of ethidium bromide which is either present in the gel or tank buffer during electrophoresis or is added after electrophoresis. The DNA is made visible by illumination with long-wave ultraviolet light. if the fragments are to be separated from the gel, an agarose is used that gels at low temperature and is obtainable from Sigma Chemical, St. Louis, Mo. After the electrophoresis, the desired fragment is cut out, placed in a plastics test tube, heated at 65° C. for about 15 minutes, extracted three times with phenol and precipitated twice with ethanol. This procedure is slightly different from that described by Maniatis et al (1982) on page 170.

As an alternative, the DNA can be isolated from the agarose with the aid of the Geneclean kit (Bio 101 Inc., La Jolla, Calif., U.S.A.).

D. Addition of synthetic linker fragments to DNA ends

If it is desired to add a new endonuclease cleavage site to the end of a DNA molecule, the molecule is optionally first treated with DNA-polymerase in order to produce blunt ends, as described in the section above. About 0.1 to 1.0 µg of this fragment is added to about 10 ng of phosphorylated linker DNA, obtained from New England Biolabs, in a volume of 20 to 30 µl with 2 µl of T4 DNA ligase from New England Biolabs, and 1 mM ATP in the buffer recommended by the manufacturer. After incubation overnight at 15° C., the reaction is terminated by heating at 65° C. for 10 minutes.

The reaction batch is diluted to about 100 µl in a buffer appropriate for the restriction endonuclease that cleaves the synthetic linker sequence. About 50 to 200 units of this endonuclease are added. The mixture is incubated for 2 to 6 hours at the appropriate temperature, then the fragment is subjected to agarose gel electrophoresis and purified as described above. The resulting fragment will then have ends with endings that were produced by cleaving with the restriction endonuclease. These ends are usually cohesive, so that the resulting fragment can then readily be linked to other fragments having the same cohesive ends.

E. Removal of 5'-terminal phosphates from DNA fragments

During the plasmid cloning steps, treatment of the vector plasmid with phosphatase reduces the recircularisation of the vector (discussed on page 13 of the Maniatis et al reference). After cleavage of the DNA with the correct restriction endonuclease, one unit of calf intestinal alkaline phosphatasc obtained from Boehringer-Mannheim, Mannheim, is added. The DNA is incubated at 37° C. for one hour and then extracted twice with phenol and precipitated with ethanol.

F. Linking of DNA fragments

If fragments having complementary cohesive ends are to be linked to one another, about 100 ng of each fragment are incubated in a reaction mixture of 20 to 40 µl containing about 0.2 unit of T4 DNA ligase from New England Biolabs in the buffer recommended by the manufacturer. Incubation is carried out for 1 to 20 hours at 15° C. If DNA fragments having blunt ends are to be linked, they are incubated as above except that the amount of T4 DNA ligase is increased to 2 to 4 units.

G. Transformation of DNA into E. coli

E. coli strain HB101 is used for most of the experiments. DNA is introduced into E. coli using the calcium chloride method, as described by Maniatis et al (1982), pages 250 and 251.

H. Screening of E. coli for plasmids

After transformation, the resulting colonies of E. coli are tested for the presence of the desired plasmid by means of a rapid plasmid isolation process. Two customary processes are described on pages 366 to 369 of the Manialls et al (1982) reference.

I. Large-scale isolation of plasmid DNA

Processes for the isolation of plasmids from E. coli on a large scale are described on pages 88 to 94 of the Maniaus et al (1982) reference.

J. Cloning in M13 phage vectors

In the following description it is to be understood that the double-stranded replicative form of the phage M13 derivatives is used for routine processes, such as cleaving with restriction endonuclease, linking etc..

Unless them is a specific indication to the contrary, enzymes can be obtained from Boehringer, Biolabs (BRL). They are used in accordance with the manufacturer's instructions unless otherwise indicated.

K. Southern blot analysis

The extracted DNA is first treated with restriction enzymes, then subjected to electrophoresis in a 0.8% to 1% agarose gel, transferred to a nitrocellulose membrane [Southern EM (1975)] and hybridised with the DNA to be detected which has previously been subjected to nick-translation (DNA-specific activities of $5 \times 10^8$ to $10 \times 10^8$ c.p.m.µg). The filters are washed three times for 1 hour each time with an aqueous solution of 0.03M sodium citmte and 0.3M sodium chloride at 65° C. The hybridised DNA is made visible by blackening an X-ray film over a period of 24 to 48 hours.

(B) AGROINFECTION OF DICOTS

EXAMPLE 1

Preparation of the bacterial vector pCa305 which contains 1,3 CaMV genomes

In the plasmid pHC79 [Hohn, B. et al, 1980], the small area between the EcoRI restriction site and the ClaI restriction site is replaced with the Eco-ClaI fragment, originating from the plasmid pMON30 [a precursor of pMON120; Fraley R. T. et al, 1983] and encoding a spectinomycin/streptomycin resistance. This is done by initially mixing plasmids pHC79 and pMON30 [0.2 µg–1.0 µg each] to a total volume of 18 µl with water. Then 2.0 µl of a 10-fold concentrated tris-HCl buffer [100 mM NaCl; 50 mM tris-Cl (pH 7.5); 10 mM $MgCl_2$; 1 mM dithiothreitol] are added. After addition of 1–5 units of each of the corresponding restriction enzymes [EcoRI and ClaI], the entire batch is thoroughly mixed and incubated for 2 to 3 hours at a temperature of 37° C.

To terminate the digestion, a 'stop' solution of the following composition is added:

| | |
|---|---|
| 4 M | urea |
| 50% | sucrose |
| 50 mM | EDTA |
| 0.1% | bromophenol blue |
| pH 7.0 | |

The fragments resulting from the digestion are resolved according to size by gel electrophoresis. The agarose gel electrophoresis is performed in a horizontal apparatus as described on pages 150–163 of the Maniails et al reference.

The buffer used is the tris-acetate buffer described therein. The DNA fragments are coloured by 0.5 µg/ml of ethidium bromide, which is either present in the gel or tank buffer during the electrophoresis or else is added after the electrophoresis. The DNA is visualised by irradiation with long-wave ultraviolet light.

If it is desired to separate the fragments from the gel, then an agarose which gels at low temperature and is available from Sugman Chemical, St. Louis, Mo., will preferably be used. After the electrophoresis, the desired fragment is excised, placed in a small plastic tube, heated for about 15 minutes to 65° C., extracted three times with phenol and precipitated twice with ethanol. This method has been slightly modified in comparison with that described by Maniatis et al (1982) on page 170.

Alternatively, the DNA can be isolated from the agarose by means of the Geneclean Kits (Bio 101 Inc., La Jolla, Calif., USA).

The DNA fragments isolated in the above described manner [the large EcoRI/ClaI fragment of plasmid pHC79 as well as the small EcoRI/ClaI fragment bearing spectinomycin/streptomycin] are incubated in a concentration of about 100 ng in a reaction mixture of 20 to 40 µl with about 0.2 units of T4 DNA ligase supplied by New England Biolabs in the buffer recommended by the manufacturer. The incubation is carried out for 1 to 20 hours at 15° C. The plasmid resulting from this ligase reaction is designated pV118.

In the pV 118 plasmid so obtained, the 2.5 kB range of plasmid pV 118be between the SalI and BstEH restriction sites is replaced with the 3.3 kB fragment which has been previously excised from CaMV "S" [Hohn, T. et al, 1982] at the SalI and BstEII restriction sites.

Plasmid pV118 is initially digested in the above described manner with SalI and BstEII. Care must be taken that the restriction enzyme BstEII employed here is preferably used in a buffer of median ionic concentration [50 mM NaCl, 10 mM tris-Cl (pH 7.5); 10 mM $MgCl_2$; 1 mM dithiothreitol]. The incubation temperature is 60° C. Simultaneous use of these two restriction enzymes is therefore not possible. Digestion is conveniently commenced with the enzyme which is incubated at lower ionic concentration, i.e. in this case with BstEII.

After digestion and separation of the fragments by gel electrophoresis, the large fragment is isolated from the gel and joined in a subsequent ligase reaction under the above stated conditions to the small 3.3 kB fragment after digestion with SalI/BstEII of the CaMV strain CaMV "S". In the plasmid pCa292 so obtained a complete CaMV CM-4184 genome [Howarth A. J. et al, 1981] is inserted into the single remaining SalI restriction site. This can be done by digesting plasmid pCa292 as well as the CaMV strain CM4184 with SalI under the conditions indicated above and then joining them together in a ligase reaction.

The plasmid pCa305, which contains 1.3 genomes of CaMV in tandem arrangement, is obtained in this manner [see FIG. 1].

EXAMPLE 2

Construction of control plasmid pEA1

To establish that the transfer of the infectious cloned virus DNA to the recipient plant has not been caused by lysis of the Agrobacterium cells, the plasmid pGV 1106 [Leeroans J. et al, 1982], which has a broad host range, is cut with the enzyme EcoRI in accordance with the above particulars and introduced into the single SphI restriction site of pCa305. The digestion of pCa305 with SphI is effected under the given conditions for the EcoRI digestion. The plasmid pEA1 so obtained is inserted into Agrobacterium tumefaciens, where it replicates independently.

Key to FIGS. 1 and 2:

| | |
|---|---|
| $Ap^R$: | ampicillin resistence |
| $Sp^R/Sm^R$: | spectinomycin/streptomycin resistance |
| ori: | origin of replication |
| bom: | origin of mobilisation |
| BstEII, SphI, SalI, EcoRI: | restriction sites |
| I-VII: | open reading frame of CaMV |
| kB: | kilobases |

EXAMPLE 3

Introduction of plasmids pCa305 and pEA1 into
Agrobacterium tumefaciens 3.1: Transformation of pCa305 and pEA 1 in E. coli GJ23

The transformation of plasmids pCa305 and pEA1 in E. coli GJ23 (pGJ28, R64drd11) [van Haute E. et al (1983)] is carried out by means of the calcium chloride method.

100 ml of a complete medium (L-medium) are inoculated with an overnight culture of E. coli host cells. The bacteria are cultivated to an optical density of 0.2 to 0.5 [≅$5\times10^7$ cells/ml] (the determination of the optical density is made at a wavelength of 650 nm). The cells are thereafter sedimented for 5 to 10 minutes [at 3000–4000×g].

The bacteria pellet is resuspended in $\frac{1}{10}$ volumes of $MgCl_2$ and sedimented once more. The sedimented bacteria are resuspended in $\frac{1}{20}$ volumes of $CaCl_2$ and kept in an ice bath for 1.5 to 8 hours. Afterwards 0.4 ml of the bacteria suspension is mixed with the plasmid DNA and the mixture is kept for a further 30 minutes in an ice bath.

The bacteria can be additionally subjected afterwards to a brief heat shock [2 min at 42° C.] and, after addition of 5 ml of liquid full medium, cultivated further for 30 minutes at 37° C. The bacteria are then sedimented once more and concentrated in 1 ml of liquid full medium. Afterwards 0.1 ml of this concentrate is streaked on L-agar which is enriched with 50 µg/ml ampicillin, 100 µg/ml streptomycin and 50 µg/ml spectinomycin [in case of pCa305] and additionally 50 µg/ml kanamycin [in case of pEA1].

3.2: Conjugal transfer

The E. coli strain GJ23 permits the conjugal transfer to Agrobacterium tumefaciens of plasmids which have a bom restriction site. The recipients are two different Agrobacterium strains which both originate from A. tumefaciens strain A136 and thus contain the wild type Ti-plasmid pTiBo542 [Hood, E. E. et al (1984)].

Cultures of the donor and recipient strains are cultivated overnight and 0.25 ml of each culture are mixed together. The bacteria are then concentrated on a 0.22 µm millipore filter which is placed on an LB-medium. The conjugation batch is incubated overnight at a temperature of 28° C. The filter is then resuspended in a λ-buffer. Selection of the exconjugants is made by plating out suitable dilutions of this suspension on selective medium.

3.3: Agrobacterium tumefaciens A136 (pTiBo542, pEAP18::pCa305)

(a) The strain *A. tumefaciens* A136 (pTiBo542, pEAP18) is used as recipient for the plasmid pCa305 (pTiBo542, pEAP18). pEAP18 is a binary vector which is constructed by starting from plasmid pGA472 [An G. et al (1985)]. Said plasmid is initially incubated with the restriction enzyme BamHI in a buffer of median ionic concentration [50 mM NaCl, 10 mM tris-Cl (pH 7.5); 10 mM $MgCl_2$; 1 mM dithiothreitol] at a temperature of 37° C. in accordance with the above description, followed by digestion with EcoRI at high salt concentration.

The EcoRI-BamHI fragment of plasmid pGA472 is replaced with the 2.6 kB EcoRI-BglII fragment of plasmid pHC79 [Hohn T. et al (1980)], which contains between the T-DNS border sequences a region for homologous recombination with the plasmid pCa305. Care must be taken that the digestion with BglII is carried out in a buffer of low ionic concentration [10 mM tris-Cl (pH 7.5); 10 mM $MgCl_2$; 1 mM dithiothreitol], at a temperature of 37° C.

As plasmid pCa305 is unable to replicate in Agrobacterium tumefaciens, selection of the exconjugants on rifampicin, spectionmycin and streptomycin affords the new strain *Agobacterium tumefaciens* A136 (pTiBo542, pEAP18::pCa305) in which the plasmid pCa305 has been integrated into the binary vector pEAP18 by homologous recombination [Leemans J. et al (1981)].

3.4: *Agrobacterium tumefaciens* A136 (pTiBo542, pEAP1)

(b) The strain *Agrobacterium tumefaciens* A136 (pTiBo542) is used as recipient for plasmid pEA1. Absorption of the plasmid pEA1, which is able to replicate independently in *Agrobacterium tumefaciens*, leads to the new strain *Agrobacterium tumefaciens* A136 (pTiBo542, pEAP1). Selection of the exconjugants is made on rifampicin (selective for *Agrobacterium tumefaciens*), kanamycin, spectinomycin and streptomycin.

The plasmids of the strains obtained as described in a) and b) above are tested by DNA isolation and restriction mapping.

(C) AGROINFECTION OF MONOCOTS

Maize Strains

For the inoculation experiments according to Examples 10, 13 and 16 the *Zea mays* varieties 'Golden Cross Bantam' (GB) and 'B73' [Grimsley et al, 1987] are used, respectively.

The inoculation experiments according to Examples 13 and 16 comprising immature maize embryos arc accomplished with the inbred line A188 (Green and Phillips, 1975), which can be obtained from T. Hein (Friedrich Miescher-Instimt, Basel, Switzerland) and can be maintained for several generations by selfing in the greenhouse; further with Inbred bx/bx, a mutant deficient in cyclic hydroxamates including DIMBOA (Coe et at., 1988; Sahi et al., 1990), which can be obtained by P. King (Friedrich Miescher-Institut) or with Inbred W23 (b, r-g background), which can be obtained from V. Chandler (University of Oregon, Eugene [Chandler et al., 1989]). The McClintock line 880254A (sul, b, R-r background) can be obtained by B. Burr (Brookhaven National Laboratory, Upton, N.Y.).

EXAMPLE 1

Construction of a vector with dimeric MSV genome

MSV-genomes can be isolated from naturally occuring infected maize plants in accordance with Mullineaux PM et al, 1984I, virion ss DNA acting as a matrix for the in vitro synthesis of double-stranded MSV-DNA using klenow-polymerase I and an endogenous primer [Donson Jet al, 1984].

Another possibility consists of the isolation of double-stranded MSV-DNA ("supercoiled MSV-DNA) directly from infected leaf material. Double-stranded MSV-DNA is formed as an intermediate during virus replication. It is referred to as "replicative form DNA" or "RF-DNA".

The MSV-genomes arc cloned by incorporating the RF-DNA or the in vitro synthesized DNA into a pUC9 vector linearised by BamHI [Vieira T and Messing T, 1982]. The lax complementation test is used to identify the recombinant phages.

The next stage in the procedure is first of all to excise the cloned MSV-DNA at the single BamHI restriction incision site. The resulting linearised DNA fragment is then isolated by gel-electrophoretic separation of the DNA mixture [Maniatis et al, (1982)].

In virus strains having two or more BamHI restriction sites, either the NSV-Genome is partially digested or another suitable restriction site is sought that appears only once in the MSV-genome. This applies also to the case where there is no BamHI restriction site in the MSV-genome.

There then follows the splicing of the BamHI fragment in tendem arrangement into the BglII restriction site of the plasmid pGA471 [An Get al, 1985], which site is located between the T-DNA border sequences. This so-called tandem-cloning can be controlled by way of the respective concentrations of vector and insert. The insert should be present in the ligation solution in excess. The preferred concentration ration is in this case 10:1 (inservector).

The plasmit pGA471 is a so-called shutfie vector, which is smbly replicated both in *E. coli* and in *Agrobacterium tumefaciens* in the presence of tetracycline.

This vector possesses, in addition to the ColE1-replication origin lying between the T-DNA border sequences, a further broad host range replication origin that makes it possible for the plasmit to be received in *Agrobacterium tumefaciens*. This replication origin originates from the plasmid pTJS75, a plasmid with a broad range of hosts and a tetracycline-resistance gene, a derivative of RK2 [An Get al, 1985].

Other characteristic properties of the plasmid pGA471 axe:

1) The possession between the T-DNA border sequences of various restriction sites that render possible incorporation of foreign DNA;

2) a cos-region of the bacteriophage λ, which permits cloning of large DNA fragments (25–35 kb);

3) a chimar marker gene, composed of the control sequences of the nopalin synthase gene (nos) and a DNA sequence coding for neomycin phosphotransferase, and also 4) a bom-incision site, which renders possible transfer of the plasmid from *E. coli* into *Agrobacterium tumefaciens*.

The above-mentioned incubation solution containing the vector and the MSV-DNA to be spliced in, preferably in a concentration ration of 1:10, is used for the transformation of the *E. coli* strain DHI [Hanahan D and Meselson M, 1980]. The selection is effected on the basis of the tetracycline resistance of the transformed clones and hybridisafion experiments using radioactively labelled MSV-DNA.

A selection of positive clones is then examined for the presence of MSV-genomes in tandem arrangement. For this purpose the plasmit DNA is isolated from the positive clones according to methods known per se [Maniatis et al, (1982)] and then subjected to restriction analysis.

One of the "tandem clones" is selected and is transferred from *E. coli* DHl to *Agrobaeterium tumefaciens* ($Rif^R$) C58 (pTiC58).

The transfer is carried out by "triparental mating", as described in detail in Rogers SG et al (1986). In this case, rifampicin (100 µg/ml) and tetraeycline (5 µg/ml) are used for the selection. The successful transfer of the dimefie MSV-genome is tested by Southern hybridisation [Dhaese P et al, 1979].

*Agrobacterium tumefaxiens* (Rif$^R$) C58 (pTiC58) [Holsters et al, 1980] contains a wild-type Ti-plasmid with intact virulence functions, rendering possible the transfer of the shuttle vector into the plant cell.

The Agrobacterium strain transformed in the manner described above has been given the fonowing strain name: *Agrobacterium tumefaciens* (Rif$^R$) C58 (pTiC58; pEAP 200).

EXAMPLE 2

Construction of a control vector

To construct a control vector without T-DNA border sequences, the plasmid pRK252 KanIII, a derivative of the plasmid pRK [Bevan M, (1984)] is used, which contains no T-DNA border sequences.

The incorporation of the dimeric MSV-genome into the control vector is carried out by splicing the above-described BamHI fragment in tandem arrangement, with the aid of a SalI/BamHI adaptor, into the SalI restriction site of the plasmit pRK252 KanIII.

The transfer of the control vector into *Agrobacterium tumefaciens* (Rif$^R$) C58 (pTiC58) is carried out by "triparental mating", as described in detail in Rogers SG al, (1986).

The transformed Agrobacterium strain has been given the following strain name: *Agrobacterium tumefaciens* (Rif$^R$) C58 (pTiC58; pEA 21 ).

EXAMPLE 3

Construction of the bacterial vector pEAP 25

By exchanging a 0.65 kb Hind III-Sal I fragment in the cosmic pHC 79, a derivative of the *E. coli* plasmid pBR322 (Hohn and Collins, 1980), for a 1.2 kb fragment from the transpose Tn 903 (Grindley et al, 1980), which carries a Kanamycin-resistance gene, the hybrid cosmic p22G1 is formed. The integration of the 1.2 kb fragment into the Hind III-Sal I restriction site of pHC 79 is rendered possible by adding Hind III-Sal I linker sequences.

A 2.9 kb Sal I-Bst EII fragment that contains a gene coding for kanamycin-resistance in plants (Paszkowski et al, 1984) is excised from the plasmid pCaMV6Km and exchanged for a 2.4 kb Sat I-Bst EH fragment from P22Gl.

The final construction of pEAP 25 is carried out by integration of the plasmid pB6 previously cut with Sal I into the Sal I incision site of pEAP 1. Plasmid pB6 wad developed and made available by J. Davies of the John Innes Institute, Norwich, England. This plasmid has since been published in N. Grimsley et al, 1987, under the name pMSV 12.

Plasmid pB6 contains a dimeric MSV-genome that has previously been cloned in the plasmid pACYC184 (Chang and Cohen, 1978).

EXAMPLE 4

Construction of the bacterial vector pEAP 37

The bacterial vector pEAP 37 is constructed by inserting the plasmid pB6, which has previously been cut with Sal I, into the Sal I restriction site of the plasmid pCIB 10. The plasmid pCIB 10 was developed and made available by Mary-Dell Chilton, CIBA-GIEGY Biotechnology Facility, Research Triangle Park, Raleigh N.C., U.S.A.

EXAMPLE 5

Manufacture of the bacterial vector pEAP 40

A 1.6 met of the MSV-genome [BglH-BamHI fragment (0.6 mer)+BamHI-BamHI-fragment, (monomer)] is spliced into the BamHI restriction sites of the plasmic pTZ19R, which is described in Mead et al (1986). The resulting plasmid, called p3547, which contains a 1.6 mer of the MSV-genome, is cut with EcoRI and then spliced into the EcoRI site of the plasmid pCIB200 (Rothstein et al, 1987). By means of these steps the MSV sequences are placed between the T-DNA border sequences of pCIB200.

EXAMPLE 6

Construction of the bacterial vector pMSV 109

5 µg of the plasmid pMSV12, the construction of which has already been described in Example 3, are digested for a period of 2 hours at a temperature of 37° C. with BamHI in a buffer solution (Maniatis et al., 1982). The 2.7 kb DNA fragment resulting from this enzymatic digestion is, after electrophoretic separation of the sample in a 1% agarose-TAE gel (40 mM tris-HCl, 20 mM sodium acetate, 2 mM EDTA), eluted from the latter and spliced into the single BamHI restriction site of the binary T-DNA vector pBin19 (Beyan, 1984).

For the ligation, a 100-fold molar excess of the 2.7 kb MSV fragment (of the "insert") in 0relation to the vector pBin19, and a high T$_4$-DNA ligase concentration, are used in order to ensure a high rate of incorporation of the dimetic MSV-DNA into the vector. in detail, the concentrations used are 625 ng of pMSV DNA and 25 ng of pBin19 DNA, which are ligated at a temperature of 10° C. for a period of 16 hours in the presence of 5 units of T$_4$-DNA ligase in a total volume of 10 µl. Half of this ligation mixture is transformed into compelend *E. coil* JM83 rec$^A$ cells, and plated out onto "Luria Broth" (LB)-agar (Maniatis et al, 1982) supplemented with 50 µg/ml of kanamycin sulphate and 40 µg/ml of 5-dibromo-4-chloro-3-indolylgalactoside (X-gat), and incubated overnight at 37° C.

White colonies that contain the MSV-insen are selected and a clone that contains the dimeric MSV-insert in tandem arrangement (pMSV109) is selected for the conjugation into *Agrobacterium tumefaciens* C58Nal$^R$ (Hepburn et al, 1985), which is carried out in accordance with a process described by Ditta et al, 1980. The selection of exconjugants is carried out on LB-agar containing 50 µg/ml of kanamycin sulphate and 50 µg/ml of nalidixic acid. The selected colony, which in the inoculation experiments described hereinafter initiates an infection in maize, is catalogued as pMSV 114.

EXAMPLE 7

Construction of a control vector (pEA 2) without T-DNA border sequences

To construct the control vector pEA 2, the Sal I restriction site of the plasmid pRK 252/kmIII, of a precursor-plasmid of pBIN19 (Bevan, 1984), is linked with the Sal I cut plasmid pB6.

The selection of pEA 2 is carried out on the basis of the kanamycin ($Km^R$)- and chloramphenicol ($Cm^R$)-resistance of the control vector.

EXAMPLE 8

Introduction of the plasmids pEAP 25, pEAP 37 and pEA 2 into *Agrobacterium tumefaciens*

The plasmid pEAP 25 is cloned in bacteria of the strain *Escherichia coli* G J23 (pGJ28, R64rd11) (van Haute et al, 1983). This *E. coli* strain renders possible the transfer by conjugation of plasmids that have abom incision site into *Agrobacterium tumefaciens*. The plasmids pEA 1, pEAP 37 and pEAP 40 are transferred via "triparental mating" into *Agrobacterium tumefaciens* (Rogers, S.G. et al, 1986). The recipient strains used are two *Agrobacterium tumefaciens* strains:

1) C58 (pTiC58) for the binary vectors pEAP 40, pEA 2 and pEAP 37

2) C58 (pTiC58), pEAP 18) for the plasmid pEAP 25.

Wild-type strains of *Agrobacterium tumefaciens* can be obtained from the "Culture Collection of the Laboratory of Microbiology, Microbiology Department of the University of Gent".

pEAP 25:

The Agrobacterium strain C58 (pTiC58, pEAP 18) acts as a recipient strain for the plasmid pEAP 25. pEAP 18 is a binary vector that is constructed by replacing the 6.7 kb EcoRI-BamHI fragment of the plasmid pGA472 (An, G. et al, 1985) by the 2.6 kb EcoRi-BglII fragment of the plasmid pHC79 (Hohn, B. et al, 1980) which contains, between T-DNA border sequences, a region for homologous recombination in the plasmid pEAP 25. Since the plasmit pEAP 25 does not replicate in *Agrobacterium tumefaciens*, the selection of the exconjugants on rifampicin, kanamycin and carbenicillin yields the new Agrobacterium strain *Agrobacterium tumefaciens* C58 (pTiC58, pEAP 29) in which the plasmid pEAP 25 has been integrated into the binary vector pEAP 18 by homologous recombination.

pEAP 37, pEAP 40

The mobilisation of the plasmide pEAP37 and pEAP40 from *E. coli* into *Agrobacterium tumefaciens* via "triparental mating" results in the construction of a binary vector system.

pEA 2

The control plasmid pEA 2 is inserted into the Agrobacterium strain C58 (pTiC58) where it establishes itself in the trans-position to the Ti plasmid already present there.

The plasmids newly constructed in the manner described above are tested by way of DNA isolation and restriction mapping.

EXAMPLE 9

Culturing the Agrobacterium strains ($Rif^R$)C58 (pTiC58; pEAP 200), ($Rif^R$) C58 (pTiC58, pEA21), C58(pTiC58, pEA 2) and C58 (pTiC58, pEAP 37), C58 (pTiC58, pEAP29); C58 (pTiC58, pEAP 40) and also C58 (pTiC58, pMSV109 and the manufacture of the inoculation solution Before inoculation, the Agrobacteria strains are plated out onto YEB medium [Bacto beef extract 5 g/l, Bacto yeast extract 1 g/l, peptone 5 g/l, sucrose 5 g/l $MgSO_4$ 2 mM, pH 7.2), which has been augmented beforehand with 100 µg/ml of rifampicin and 25 µg/ml of kanamycin or 50 µg/ml of nalidixic acid and solidified with 1.5% agar. After a culturing period of 48 h at a temperature of 28° C., a single colony is used to inoculate a liquid culture. The inoculation is carried out in 100 ml Erlenmeyer flasks in a liquid YEB medium that has been augmented with antibiotics in the afore-mentioned concentration. Culturing is carried out at a temperature of 28° C. on a stirring machine at a speed of 200 r.p.m. The culturing period is 24 h.

Then, a second sub-culturing process is carried out in liquid medium at a dilution ratio of 1:20 under otherwise identical conditions. The incubation period is in this case 20 h.

These steps lead to a population density of living agrobacteria of approximately $10^9$/ml.

The bacteria cells are harvested by centrifuging and are then resuspended in an equivalend volume of a 10 mM $MgSO_4$ solution that does not contain any antibiotics.

This suspension is referred to as an undiluted strain solution in the following procedure. When preparing a series of dilutions, 10 mM $MgSO_4$ solution is again used as diluent.

EXAMPLE 10

Sterilisation and germination of maize seeds

For the inoculation experiments plants of the varieties Golden Cross Bantam, B 73, North Star and/or Black Mexican Sweetcorn are used, all of which can be successfully agroinfected.

For the following experiments, as a rule 3-day-old, previously sterilised seedlings are used. The stefilisation of the seedlings comprises the following process steps:

1. Sterilisation of the seeds in a 0.7% w/v calcium hypochlorite solution (250 ml solution/100 seeds). The seeds and solution are thoroughly mixed using a magnetic stirrer.

After 20 minutes the sterilisation solution is decanted.

2. The seeds treated in this manner are then washed 3 times with distilled water (250 ml dist. water/100 seeds) for 30 minutes each time.

The seeds sterilised in this manner are then introduced into seed chambers that have also already been sterilised. The seed chambers are peri dishes which each contain 3 sterile Macherey-Nagel® round filters having a diameter of 8.5 cm and also approximately 10 ml of sterile water.

20 seeds are introduced into each of these seed chambers and incubated in the dark for approximately 3 days at a temperature of 28° C.

For the subsequent inoculation experiments, only seedlings in which the distance between scutellar node and the apical coleoptile tip is 1–2 cm are used in any case, however, it must be ensured that the coleoptile node is clearly identifiable.

EXAMPLE 11

Immature Embryo Production, Isolation, and Cultivation

The maize seeds used are obtained from the lines listed in Table 7. All seeds are surface sterilized in 1,4% sodium hypochlorite for 20 rain and washed three times in sterile water. Aseptic seeds are germinated on wet filter paper in Petri dishes at 28° C. for 3 days in the dark. Seedlings are propagated subsequently in small pots in a plant growth chamber under 16-hr light, 25° C., and 8-hr dark, 20° C., 20,000 lux light regime with 50% humidity. After 2 to 3 weeks, well-grown seedlings are transferred into 20-liter pots containing slow-release fertilizer and propagated under the same light/dark regime. Alternatively, seedlings are transferred into a greenhouse field and propagated under similar light conditions. After 2 to 2.5 months, emerging ears are bagged and the husks cut back as soon as the first silks appeared. One day later, newly emerging silks are pollinated with fresh pollen of either the same (selfed) or another plant of the same genotype (sibbed). Pollinated ears are protected with "Lawson" bags obtained from Funk Seeds (Bloomington, Ill.). lmmamre ears are harvested at the desired DAP, and immature kernels are removed, surface sterilized for 20 min in 1.4% sodium hypochlorite, and washed three times in sterile water.

Immature embryos are excised aseptically in a laminar flow bench using sterilized forceps and scalpels. Embryos smaller than 1 mm in length are removed with the help of a stereomicroscope. Excised embryos are placed with the scutellar side down onto 1% agar solidified MS medium (Murashige and Skoog, 1962) containing 3% sucrose and 1 mg/liter thiamine-HCl. Per plate, 30 to 50 immature embryos are either inoculated immediately after isolation or germinated up to 3 days in the dark at 25° C. for 16 hr, followed by 8 hr at 20° C.

Immature embryos derived from one cob are always distributed onto four MS plates. One plate is inoculated immediately after embryo isolation, the others are inoculated 1, 2, and 3 days after germination, respectively. Excised mature embryos from sterilized seeds for control inoculations are treated in the same way.

EXAMPLE 12

Inoculation of the maize seedlings

Hamilton hypodermic syringes (A 50 µl or 100 µl) fitted with exchangeable needles 0.4 mm in diameter are used to introduce the inoculation solution described under point 3. into the maize seedlings.

The inoculation solution is taken up into the hypodermic syringe in such a manner that no air bubblers are formed.
12.1 Inoculation of 10-day-old maize plants The inoculation of the bacteria-containing suspension into 10-day-old maize plants is carried out by various methods and at different sites on the plant.

1. Application of 20 µl of bacterial suspension to one of the upper leaves and rubbing the suspension into the leaf with the aid of carborundum powder until the entire leaf appears wet (position A in diagram 1).
2. Injection of 10 µl of the bacterial suspension using a 100 µl Hamilton hypodermic syringe into the central pan of the plant
   a) exactly above the ligula of the primary leaf (position B in diagram 1)
   b) 1 cm below the ligula of the primary leaf (position C in diagram 1)
   c) at the base of the plant in the so-called root collar, a meristematic tissue from which adventitious roots later develop (position D in diagram 1).

12.2 Inoculation of 3-day-old maize seedlings

The inoculation of the bacterial suspension into 3-day-old maize seedlings is carried out by injection into the seedling using a 100 µl Hamilton hypodermic syringe.

1. Injection of the bacterial suspension into the coleoptilar node by introducing the hypodermic needle through the coleoptile, starting from the apical coleoptile tip and passing into the region of the coleoptilar node (position E in diagram 2).
2. Injection of the bacterial suspension directly into the coleoptile, 2 mm below the apical coleoptile tip (position F in diagram 2).
3. Injection of the bacterial suspension directly into the coleopfile, 2 mm above the coleoptile node (position G in diagram 2).
4. Injection of the bacterial suspension directly into the coleoptilar node (position H in diagram 2).
5. Injection of the bacterial suspension directly into the coleoptile, 2 mm below the coleoptilar node (position I in diagram 2).
6. Injection of the bacterial suspension directly into the scumliar node (position J in diagram 2).
7. Injection of the bacterial suspension into the scutellar node (by introducing the hypodermic needle through the primary root, starting from the root tip and passing into the region of the scutellar node (position K in diagram 2).

12.3 Decapitation of the coleoptile in the region of the coleoptilar node 3-day-old maize seedlings are decapitated at various points in the region of the coleoptilar node (see diagram 3).

1. 1 mm above the coleoptilar node
2. 2 mm above the coleoptilar node
3. 5 mm above the coleoptilar node.

The decapitated seedlings are then planted in moist earth and cultivated in accordance with the conditions given under point 6.

The actual inoculation experiments with Agrobacterium are carried out on seedlings in which the coleopfile tips above, in preparation, been removed 2 mm above the coleoptilar node.
12.4 Cultivating the treated maize plants and maize seedlings Directly after the inoculation treatment the maize seedlings are planted in moist earth and cultivated in the same manner as the 10-day-old maize plants at a temperature of 22° C. ±° C. with permanent lighting with white (Phillips 400 W/G/92/2) at 3000–5000 lux.

The plants are then examined daily for the presence of symptoms of a virus infection, which is characterised by the appearance of yellow dots and/or streaks at the base of newly formed leaves.

EXAMPLE 13

Inoculation of Immature Embryos

The apical meristem or the shoot apex of immature embryos as small as 1 mm is punctured with a Microlance 26G$^3$/8 0.45×10 fine needle, and the smaller embryos are punctured with a drawn out µlass microcapillary. Immediately after puncturing, 2 to 4 µl of an overnight Agrobacterium culture containing the MSV construct according to Example 5 is applied. Bacteria are obtained with a liter of 10⁹ cells per milliliter, washed, and resuspended in 10 mM MgSO$_4$ to the same concentration. Successive subcultivations are done up to 3 days for each germination series. After every subcultivation step, the presence of correct pLE1 sequences is tested by restriction analysis after plasmid isolation by an alkaline lysis procedure (Sambrook et al., 1989). Inoculated immature embryos are incubated with the apicai side on the MS medium for 24 hr in the dark, then flipped over and incubated for another day on the same medium under 16-hr light, 10,000 lux, 25° C. followed by an 8-hr dark, 20° C. regime. Embryos are then transferred onto 0.8% agar solidified MS medium containing 3% sucrose, 1 mg/liter thiamine-HCl, 500 µg/ml cefotaxim (Hoechst, Frankfurt, Germany), and 500 µg/ml carbenicillin against Agrobacterium growth. After 1 week, immature planfiets are transferred into Magenta boxes containing MS medium solidified with 0.8% agar and containing 2% sucrose and 1 mg/liter thiamine-HCl. Twelve DAP immature embryos from the line B73 (Funk seeds) are inocuolated with Agrobacterium preinduced with acetosyringone.

EXAMPLE 14

Scoring for MSV Symptoms 14.1: DNA extraction from infected, symptomatic maize plants Approximately 400 mg (fresh weight) of young leaf tissue is first of all homogenised in a mortar on ice, with the addition of 0.5 ml–1,0 ml STEN (15% sucrose, 50 mM tris-HCl, 50 mM Na$_3$ EDTA, 0.25M NaCl, pH 8) and sand (~50 mg) to assist the tissue digestion. The homogenisate is then transferred into a small centrifugation robe (1.5 ml) and centrifuged for 5 minutes at a temperature of 4° C. in a table centrifuge at maximum speed. The supernatant is discarried and the pellet is resuspended in 0.5 ml of ice-cold SET (15% sucrose, 50 mM Na$_3$ EDTA, 50 mM tris-HCl, pH 8) while stirring first of all with a sterile toothed rod, and then briefly using a vortex mixer (5 seconds). Subsequently, 10 µl of a 20% SDS solution and 100 µl of proteinase K (20 mg(ml) are added and mixed in and the whole is then heated in the small tube for 10 minutes at 68° C. After the addition of 3M sodium acetate (1/10 volume) the lysate is extracted twice with phenol/chloroform (3:1). The DNA is then precipitated by the addition of 2 parts by volume of ethanol and stored overnight at −20° C. Centrifugation (10 min.) in a table centrifuge at maximum speed yields a DNA-containing pellet which is subsequently dissolved in 40 µl of TE buffer (40 mM tris-HCl, 1 mM Na$_3$ EDTA, pH 8).

Aliquots of this DNA solution are used for the "Southern blot" experiments (Southern EM, 1975).
14.2: Vir Gene Induction Assays Immature shoots were scored 2 to 4 weeks after inoculation for MSV symptom formation. With the exception of the mutant bx/bx, between 45 and 95% of the inoculated immature embryos, depending on age and genotype, survived the inoculation procedure. Within a germination series, ungerminated immature embryos had higher survival rates than germinated embryos. Control inoculations with 10 mM MgSO$_4$ gave similar survival results. Therefore, the frequency of symptom formation was calculated as the fraction of shoots with MSV symptoms per total surviving shoots.

Induction of an Agrobacterium vir gene by immature embryos was measured qualitatively, as described by Grimsley et al (1989). An Agrobacterium strain with a lacZ insertion in the pinF ("plant inducible") locus of the Ti-plasmid virulenee region was grown in YEB medium supplemented with 100 µg/ml carbenicillin overnight at 28° C., subcultured into 1XM9 medium (Miller, 1972) supplemented with 100 µg/ml carbenicillin overnight at 28° C., then diluted to OD$_{600}$=0.1 in 1×M9 medium. One microliter 2% 5-bromo-4-chloro-3-indole-galactose (X-Gal; Sigma) in dimethyl-formamide was added to 500 µl of bacterium suspension, and cocultivation with wounded immature embryos was done overnight at 28° C. with 100 µl in a microtiter dish. Acetosyringone (Sigma) in a final concentration of 100 µM, added to the bacterium suspension, was used as a positive control. Blue spots on immature embryos and blue medium were scored as inducing the pinF gene.
14.3: Histological Analysis of Immature Embryos Embedding, thin sectioning, and staining with hematoxylin or safranin/fast-green was done using standard procedures (Grimsely et al, 1988)

EXAMPLE 15

"Southern blot" analysis

The extracted DNA is first of all treated with restriction enzymes and then subjected to electrophoresis in 1% agarose gel, transferred onto a nitrocellulose membrane [Southern, (1975)] and hybridised (DNA-specific activities of 5×10⁸ to 10×10⁸ c.p.m./µg) with the DNA to be detected, which was previously been subjected to a nicktranslation [Rigby et al,]. The filters are washed three times for an hour each time with an aqueous solution of 0.03M sodium citrate and 0.3M sodium chloride at 65° C. The hybridised DNA is made visible by blackening an X-ray film for from 24 to 48 hours.

EXAMPLE 16

T-DNA Transfer to Maize Cells 16.1: Plasmid constructions, bacterial strains and culture conditions.

The GUS gene used here has first been described by Schultze et al (1990). The plasmid pGUS23, containing this GUS gene in the pUC7 vector, has also been described previously in Puchta and Hohn (1991). Plasmid pBG5 is constructed by cloning the GUS gene-containing EcoRI fragment of pGUS23 into the EcoRI site of the binary vector pBIN19 [Bevan (1984); see also Example 6]. The HindIII fragment containing the same GUS gene of pGUS23 is also cloned into the HindIII site of the binary vector pCGN1589, described in McBride and Summerfelt (1990), resulting in plasmid pCG5. Plasmids are maintained in E. coli strain DHSot and isolated as described hereinbefore.

Plasmdis pBG5 and pCG5 are introduced into different A. tumefaciens strains using the triparental-mating method of Rogers et al (1988). Table 1 lists Agrobacterium strains used.

The Agrobacterium strain C58C1 is described in Holsters et al (1980).

The Agrobacterium strain LBA4301 [pJK270] is described in Klapwijk et al (1979) and in Rogowsky et al (1987).

The Agrobacterium strains LBA4301 [pJK190, pCG5] and LBA4301 [pJK210, pCG5][Rogowsky et al (1987)] are two different virB mutants, that are deficient in an essential step in T-DNA transfer, and are used, therefore, as controls.

The Agrobacterium strains are grown in shaking liquid cultures at 28° C. for 48h in YEB medium [as to its' composition see Example 9] supplemented with appropriate antibiotics. They are subcultured in the same medium following a 1:20 dilution, and grown for a further 20 h, reaching a final titre of $1-2\times10^9$ cells/ml. Cells are then harvested by centrifugation, washed with 10 mM $MgSO_4$ and resuspended in 10 mM $MgSO_4$ or in MS medium [Murashige & Skoog (1962)] to a final titre of $1-2\times10^{10}$ cells/ml.

16.2: Preparation of maize shoots

Maize lines Golden Cross Bantam (GB) and A188 are previously described [see Part B, Maize lines]. Line K55 was provided by Dr. V. Walbot (Department of Biological Sciences, Stanford University). GB seeds and immature kernels of A188 and K55 harvested 14–17 days after pollination are surface sterilized in 1.4% sodium hypochlorite and 0.05% SDS for 20 min and washed 3 times for 5 min each in sterile water. Seeds are germinated on water-wet filter paper at 28° C., in the dark. Embryos are isolated from immature kernels and germinated on agar MS medium in a phytotron under a regime of 16 h light (20 000 lux) and 8 h dark, at 25° C. Shoots are isolated from seedlings by cutting just below (about 1–3 mm) the coleoptilar node where the shoot meristem is located.

16.3 Cocultivation of maize shoots with Agrobacterium

Acetosyringone (AS), a substance known to induce the expression of vir genes of Agrobacterium and initiate processes leading to transformation, is added at a final concentration of 200 μM to Agrobacterium suspension, just before the cocultivation with maize shoots. The shoots are dipped into Agrobacterium suspension and subjected to vacuum infiltration (–0.4 to –0.6 Atm) for 5 min. The infiltrated maize shoots are cultured on the agar plates of MS medium supplemented with 200 μM AS, in the phytotron under the same condition as for germination of immature embryos. The shoots are collected for GUS staining assay 3 days after cocultivation with Agrobacterium.

16.4: Activity assay for β-glucuronidase

Maize shoots are soaked with 0.052% 5-bromo-3-chloro-3-indolyl glucurpmode (X-Gluc) in 100 mM $NaH_2PO_4$, pH 7.0, in the presence of 0.1% sodium azide. After 10 min of vacuum infiltration, the reactions are continued at 37° C. for two days in the dark. Shoots are destained for chlorophyll by rinsing with ethanol (70–90%).

(D) RESULTS

A) Inoculation of 10-day-old maize plants

Table 1 shows the results of inoculation experiments on 10-day-old maize plants described under point 10.1. The inoculation is carried out using pEAP 37 DNA.

TABLE 1

| inoculation site | number of plants with symptoms/ number of inoculated plants | | pEAP 200 | pEAP 25 |
|---|---|---|---|---|
| | pEAP 37 | pMSV 109 | | |
| A | 0/46 (<2%) | — | — | — |
| B | 0/44 (<2%) | — | — | — |
| C | 3/46 (6.5%) | — | + | + |
| D | 42/68 (62%) | 26/65 (40%) | ++ | ++ |

The results in Table 1 show clearly that the preferred site of application on the plant is located in the region of the root collar, where 62% and 40% of the treated plants exhibit symptoms of infection, whilst the number of plants exhibiting symptoms of infection after being inoculated at the other inoculation sites on the plant (A, B, C) is 0 or negligibly small.

B) Inoculation of 3-day-old maize seedlings

Tabel 2 shows the results of inoculation experiments on 3-day-old maize seedlings described under point 10.2. The inoculation is carried out using pEAP 37 and pEAP 40 DNA.

TABLE 2

| | number of plants with symptoms/ number of inoculation plants | |
|---|---|---|
| inoculation site | pEAP 37 | pEAP40 |
| E | 21/27 (78%) | — |
| F | 0/20 (<5%) | — |
| G | 3/19 (16%) | — |
| H | 25/30 (83%) | 51/58 (88%) |
| I | 8/51 (16%) | — |
| J | 1/20 (5%) | — |
| K | 2/12 (17%) | — |

As the results in Table 2 show, the preferred site of application on the maize seedling is in the region of the coleoptile node, direct and indirect application of the bacterial suspension directly into the coleoptile node, with 83% and 88% or 78% of the plants becoming infected, being clearly preferred by comparison with all other application sites investigated. Whether the suspension is injected directly into the coleoptile node laterally, or is injected indirectly through the coleoptile, is clearly of no significance.

C) Decapitation of 3-day-old maize seedlings.

Table 3 shows the number of surviving seedlings 2 weeks after decapitation of the coleoptile at various sites in the region of the coleoptile node.

TABLE 3

| inoculation site | number of surviving seedlings/ number of decapitated seedlings |
|---|---|
| 1 | 0/7 |
| 2 | 5/8 |
| 3 | 8/8 |
| 4 | 8/8 |

It can be seen that the plumule can be removed up to 2 mm above the coleoptile node without any impairment of the viability of the seedlings treated in this manner being observed. Even removal of the plumul only 1 mm above the coleoptile node still results in approximately 60% of cases in completely viable plantlets.

Table 4 shows the results of inoculation experiments on redlings decapitated 2 mm above the coleoptile node. The inoculation is carried out using pEAP 37 DNA.

TABLE 4

| inoculation site | number of plants with symptoms/ number of inoculated plants |
|---|---|
| L | 48/49 (98%) |
| M | 14/44 (32%) |

The results in Table 4 show clearly that position L on the decapitated seedling, that is to say the meristematic tissue region, is distinctly preferred to position M, which covers the peripheral area of tissue.

D) Dilution experiments

The bacterial suspension described under point 9 is diluted in YEB medium without the addition of antibiotics and applied into the coleoptilar node in the concentrations indicated below.

| dilution | estimated number of bacteria remaining in the inoculation site | number of plants with symptoms/ number of inoculated plants |
|---|---|---|
| undiluted | $2 \times 10^6$ | 84/102 (82%) |
| $10^{-1}$ | $2 \times 10^5$ | 42/55 (76%) |
| $10^{-2}$ | $2 \times 10^4$ | 34/54 (62%) |
| $10^{-3}$ | $2 \times 10^3$ | 19/56 (34%) |
| $10^{-4}$ | 0 | 0/10 (<10%) |
| $10^{-5}$ | 0 | 0/10 (<10%) |

Assuming that the number of copies of the binary vector that contains the MSV sequences is approximately 10 and that the bacteria do not increase further in the inoculation site, $10^4$ bacteria contain approximately 400 fg ($4 \times 10^{13}$ g) of MSV-DNA.

This means that Agrobacterium transfers its DNA to maize with an efficiency comparable to that with which it transfers its DNA to dicotyledonous host plants.

E) Agrobacterium host range

Apart from maize, it was possible to ascertain other representatives from the Gramineae class that are accessible to infection by Agrobacterium.

The results of inoculation experiments with these Gramineae species are shown in Table 5:

TABLE 5

| Gramineae species | number of plants with symptoms/ number of inoculated plants |
|---|---|
| barley (Maris Otter) | 1/15 (6%) |
| wheat (Maris Butler) | 1/40 (2%) |
| wheat (normal) | 1/25 (4%) |
| spring oats (Saladin) | 1/25 (4%) |
| Panicum milaceum | 3/8 (35%) |
| Digitaria sanguinalis | 2/10 (20%) |
| Lolium temulentum | 1/25 (4%) |

Some of the less effective results are possibly attributable to technical difficulties arising in the course of inoculation, since the plants are in some cases very small and therefore have only small stem diameters, which makes a specifically targeted injection of the inoculation solution difficult.

This apart, the results above show that, besides maize, it is possible to transform a number of other representatives from the Gramineae group by means of Agrobacterium.

F) Agrobacterium strains

In addition to the *Agrobacterium tumefaciens* strain C58 routinely used in the inoculation experiments with maize, other *A. tumefaciens* and *A. rhizomes* strains are also tested. It was also possible using the following Agrobacterium strains listed in Table 6 to detect transfer of MSV-DNA to maize:

TABLE 6

| Agrobacterium strain | number of plants with symptoms/ number of inoculated plants | |
|---|---|---|
| | pMSV 109 *1 | pEAP 37 *2 |
| *A. tumefaciens* | | |
| T 37 | 3/6 (50%) | 6/6 (100%) |
| LBA 4301 (pTiC58) | 21/23 (91%) | 15/21 (71%) |
| A 6 | 0/8 (<1%) | 2/37 (5%) |
| *A. rhizogenes* | | |
| R 1000 | 17/22 (81%) | — |
| LBA 9402 | 15/20 (75%) | — |
| 2626 | 7/12 (51%) | — |

*1 The inoculation experiments with pMSV 109 are carried out on 10-day-old maize plants
*2 The inoculation experiments with pEAP 37 are carried out on 3-day-old maize seedlings.

TABLE 7

Agroinfection Frequencies* of Seedlings and In Vitro Germinated Mature Embryos

| Maize Line | In Vitro-Germinated Excised Mature Embryos [%] | 3-Day-Old Seedlings [%] |
|---|---|---|
| A188 | 81 | 90 |
| bx/bx | 57 | 52 |
| W23 | 33 | 53 |
| 880254A | 53 | 30 |

*Frequencies of MSV symptom formation are determined 3 weeks after inoculation by calculating the fraction of shoots showing MSV symptoms per total surviving (germinating) shoots.

TABLE 1

Characteristics of Agrobacterium strains used for transformation of maize

| Strain | Chromosome | Virulence genes | Binary vector |
|---|---|---|---|
| C58C1 (pBG5) | nopaline wild-type C58C1 | none | GUS gene in pBIN19 |
| C58C1 (pTiC58, pBG5) | nopaline wild-type C58C1 | pTiC58: a nopaline wild-type Ti plasmid | GUS gene in pBIN19 |
| C58C1 (pTiC58, pCG5) | nopaline wild-type C58C1 | " | GUS gene in in pCGN1589 |
| LBA4301 (pJK270, pCG5) | octopine-type Ach5 derivative | pJK270 containing the full set of C58 virulence genes | GUS gene in in pCGN1589 |
| LBA4301 (pJK190, pCG5) | octopine-type Ach5 derivative | pJK190, differing from pJK270, by a polar Tn5 insertion in vir B4 | GUS gene in in pCGN1589 |
| LBA4301 (pJK210, pCG5) | octopine-type Ach5 derivative | pJK210, differing from pJK270, by a non-polar Tn5 insertion in vir B10 | GUS gene in in pCGN1589 |

TABLE 2

GUS expression detected on shoots of maize seedlings germinated from immature embryos, after cultivation with Agrobactrium

| Agrobacterium | maize | No. of shoots tested | No. of shoots showing blue spots | % of shoots showing blue spots | Total no. of blue spots | Average no. of blue spots per shoot |
|---|---|---|---|---|---|---|
| A. | | | | | | |
| LBA4301 (pJK190, pCG5) | A188, 14 DAP | | | | | |
| | 5 DAG | 41 | 13 | 32 | 266 | 6.4 |
| | 8 DAG | 62 | 18 | 29 | 263 | 4.2 |
| | K55, 14 DAP | | | | | |
| | 5 DAG | 54 | 0 | 0 | 0 | 0 |
| C58C1 (pBG5) | A188, 14DAP | | | | | |
| | 5 DAG | 37 | 0 | 0 | 0 | 0 |
| | 8 DAG | 60 | 0 | 0 | 0 | 0 |
| B. | | | | | | |
| C58C1 (pTiC58, pBG5) | A188, 17 DAP | | | | | |
| | 5 DAG | 33 | 24 | 73 | 1031 | 31.2 |
| C58C1 (pTiC58, pCG5) | A188, 17 DAP 5 DAG | 43 | 14 | 32 | 236 | 5.5 |
| LBA4301 (pJK270, pCG5) | A188, 17 DAP 5 DAG | 54 | 7 | 13 | 96 | 1.8 |
| LBA4301 (pJK190, pCG5) | A188, 17 DAP 5 DAG | 56 | 0 | 0 | 0 | 0 |
| LBA4301 (pJK210, pCG5) | A188, 17 DAP 5 DAG | 55 | 0 | 0 | 0 | 0 |

DAP: days after pollination; DAG: days after germination.

(E) DEPOSITS

The plasmids used within the scope of the present invention, pEAP 37, pEAP 40 and pMSV 109, were deposited at the "Deutsche Sammlung von Mikroorganismen" (DSM), in Göttingen, Federal Republic of Germany and "The National Collection of Industrial Bacteria" (NCIB), Torry Research Station, P.O. Box 31, 135 Abbey Road, Aberdeen, both recognised as International Depositories in accordance with the requirements of the Budapest Treaty on the international recognition of the deposit of microorganisms for the purposes of patent procedure. A declaretion regarding the biability of the deposited samples was prepared by the said International Depositories.

| microorganisms | deposition date | deposition number | date of the viability certificate |
|---|---|---|---|
| pEAP 37 (Escherichia coli DH1 transformed with pEAP 37 plasmid-DNA) | 16 June 1987 | DSM 4147 | 19 June 1987 |
| pEAP 40 (Escherichia coli DH1 transformed with pEAP 40 plasmid-DNA) | 16 June 1987 | DSM 4148 | 19 June 1987 |
| pMSV 109 (Escherichia coli JM 83 RecA transformed with pMSV 109 plasmid-DNA) | 23 Sept. 1987 | NCIB 12547 | 24 Sept. 1987 |

Limitations on the availability of the said microorganisms have not been requested by the depositor.

(F) BIBLIOGRAPHY

An, G. et al, EMBO J 4, No. 2, 277–284, 1985

Bevan M, Nucl. Acids Res 12 204–207, 1984

Coe et al, The Genetics of Corn, in: Corn and Corn Improvement, eds. Sprague G. F. and Dudley J. W. (Madison, Wis.: American Society of Agriculture), pp 81–258, 1988

Chandler et al, Plant Cell 1, 1175–1183, 1989

Chang A. C. Y. and Cohen S. N., J Bacteriol 134, 1141–1156, 1978

Cress et al, Nucl Acids Res 11, 6821–6835, 1983

DeCleene M., Phytopath Z. 113, 81–89, 1985

Dhaese P. et al, Nucleic Acids Res 7, 1837–1849, 1979

Ditta G. et al, Proc Nail Acad Sci, USA 77(12), 7347–7351, 1980

Donson J. et al, EMBO J 3(13), 3069–3073, 1984

Fraley, R. T. et al, Proc Nail Acad Sci, USA 80, 4803–4807, 1983

Frank G. et al, Cell, 21: 285–294, 1980

Fromm M. et al, Proc Natl Acad Sci, USA g 5824–5828, 1985

Gardner R. C. et al, Nucl. Acids Res., 9:2871–2888 (1981)

Graves A. C. F. and Goldman S. L., J Bacteriol 169(4), 1745–1746, 1987

Green and Phillips, Crop Sci 15,417–421, 1975

Grimsley N. H., et al, Nature, 325(8), 177–179, 1987

Grimsley N. H., et al, Bio/Technology 6, 185–189, 1988

Grimsley N. H., et al, Mol Gen Gent 217, 309–316, 1989

Grindley N. D. F., et al, Proc Natl Acad Sci, USA 77, 7176–7180, 1980

Hain et al, Mol Gen Genet 199, 161–168, 1985

Hanahan D. and Meselson M., Gene g 63–67, 1980

Hepburn et al, J Gen Microbiol 131, 2961–2969, 1985

Hernalsteens J. P. et al, EMBO J 3, 3039–41, 1984

Hohn, B. et al, Gene 11, 291–298, 1980

Hohn, T. et al, Current Topics of Microbiology 96, (ed. Henle et al), 193–236, Springer-Verlag Berlin, 1982

Hohn T. et al, in: "Molecular Biology of Plant Tumors", Academic Press, New York, pp. 549–560 (1982)

Hohn, B. and Collins, J., Gene 11, 291–298 1980

Hood, E. E. et al, Bio/Technology, August 1984
Hooykaas-Van Slogteren GMS et al, Nature 311,763–764, 1984
Holsters et al, Plasmid 3, 212, 1980
Howard et al, Planta, 170, 535, 1987
Howarth, A. J. et al, Virology 112, 678–685, 1981
Howell et al, Science 208, 1265–1267, 1980
Jacob, F. et al, Cold Spring Harbor Symp. 28, 329, 1963
Kegami M., et al, Proc Natl Acad Sci, USA 78, 4102, 1981
Kapwijk et al, Mol Gen Genet 173, 171–175, 1979
Lebeurier et al, Proc Natl Acad Sci, USA 79, 2932–2936, 1982
Leemans, J. et al, Genet. 1, 149–164, 1981
Leemans, J. et al, Gene 19, 361–364, 1982
Lörz H. et al, Mol Gen Genet 119, 178–182, 1985
McBride and Summerfelt, Plant Mol Biol 14, 269–276, 1990
Maniatis et al, Molecular Cloning, A Laboratory Manual, Cold Spring Harbor, (1982)
Mead D. A., et al, Protein Engineering 1, 67–74, 1986
Morikawa H. and Yamada, Plant Cell Physiol 26, 229–236, 1985
Moreili et al, Nature, 315, 200, 1985
Mullineaux, P. M., EMBO J 3, No. 13, 3063–3068, 1984
Mullineaux P. M. et al, EMBO J 3(13), 3069–3073, 1984
Pareddy D., et al, Planta 170, 141–143, 1987
Paszkowski J. et al, EMBO J 3, 2717–2722, 1984
Potrykus I. et al., (1985a) "Direct gene transfer for protoplasts: an efficient and generally applicable method for stable alterations of plant genoms", In: Freeling M. (ed.), *Plant Genetics* Alan R. Liss Inc., New York, pp 181–199
Puchta and Hohn, Nucl Acids Res 19, 2693–2700, 1991
Rigby W. J. et al, J.Mol. Biol. 113, 237–251, ?
Rogers, S. G. et al, Methods in Enzymology 118, 630–633, 1986
Rogers et al, In: Plant Mol Biol Manual, eds. Gelvin & Schilperoort (Dordrecht: Kluwer Academic Publishers), pp. A2: 1–12, 1988
Rogowsky et al, J Bacteriol 169, 5101–5112, 1987
Rothstein S. J. et al, Gene, 53, 153–161, 1987
Sahi et al, Proc Natl Acad Sci, USA 87, 3879–3883, 1990
Sambrook J et al, Molecular Cloning: A Laboratory Manual (Cold Spring Harbor, N.Y.; Cold Spring Harbor Laboratory) 1989
Schultze et al, EMBO J 9, 1177–1185, 1990
Shewmaker et al, Virology 140, 281–288, 1985
Southern, E. M., J Mol Biol 98, 503–517 1975
Spena et al, EMBO J., 4, 2736, 1985
Stachei et al, Nature 318, 624–629, 1985
Steinbiss H. H. and Stabel P., Protoplasma 116, 223–227; 1983
Van Haute, E. et al, EMBO J. 2, No. 3, 411–417, 1983
Vasil I. K., Cell Culture and Somatic Cell Genetics of Plants, Vol. 1, ed. I. K. Vasil, Academic Press, 1984
Vieira T. and Messing T., Gene 19 259–268, 1982
Zambryski, A., Ann Rev Genetics, 22, 1–30, 1988

Patent literature

WO 89/11291
WO 86/04356
WO 88/05826
U.S. Pat. No. 4,810,777
WO 89/04371
EP-A 462,065
EP-A 392,225

What is claimed is:

1. A method of transforming plants with cloned viral DNA, wherein said cloned viral DNA, normally not infectious upon mechanical inoculation, is amenable by this method for transformation by a transfer microorganism of the genus Agrobacterium, which method comprises (a) inserting cloned viral DNA capable of giving rise to a systemic infection and that may contain cargo DNA, into a T-replicon of an Agrobacterium, having one or more T-DNA border sequences, wherein the distance between said cloned viral DNA and the T-DNA border sequences is chosen such that cloned viral DNA, including any cargo DNA present, is genetically transferred to the plant material;

(b) introducing the T-replicon into a transfer microorganism of the genus Agrobacterium, the replicon passing into the transfer microorganism;

(c) preparing a microorganism-containing transforming suspension culture comprising the transfer microorganism obtained in step (b); and (d) infecting plant material with the transfer microorganism that has been modified in accordance with step (b).

2. A method according to claim 1, wherein the T-replicon comprises more than one cloned viral DNA.

3. A method according to claim 2, wherein the cloned viral DNA is arranged in a tandemly duplicated form.

4. A method according to claim 1, wherein the cloned viral DNA is inserted between the T-DNA border sequences.

5. A method according to claim 1, wherein said cloned viral DNA is selected from the group consisting of (a) double-stranded DNA forms of single-stranded DNA viruses and functional parts thereof;

(b) cDNA copies of viral RNA or viroid RNA and functional parts thereof;

(c) any viable mutants of viruses and functional parts thereof; and (d) portions of viral DNA that are still capable of giving rise to a systemic infection.

6. A method according to claim 5, wherein the double-stranded DNA forms of single-stranded DNA viruses and functional parts thereof are from Gemini viruses.

7. A method according to claim 6, wherein said Gemini virus is a Maize Streak virus (MSV).

8. A method according to claim 5, wherein the cDNA copies of viral RNA or viroid RNA and functional parts thereof are from a Tobacco-Mosaic virus or a Cadang-Cadang viroid.

9. A method according to claim 1, wherein the cloned viral DNA or the functional equivalents thereof comprises cargo DNA which has been inserted therein.

10. A method according to claim 9, wherein the said cargo DNA is of either homologous or heterologous origin or is prepared by synthetic means.

11. A method according to claim 9, wherein said cargo DNA comprises a chimeric DNA construct comprising an expressible DNA in operable linkage with expression signals active in plant cells, such as promoter and termination sequences, as well as, optionally, further coding and/or non-coding sequences of the 5' and/or 3' region.

12. A method according to claim 11, wherein said expressible DNA comprises a structural gene.

13. A method according to claim 12, wherein said structural gene, upon expression, leads to a protective effect in the transformed plant.

14. A method according to claim 13, wherein said structural gene, upon expression, leads to resistance against plant pathogens selected from the group consisting of insects, fungi, bacteria and viruses.

15. A method according to claim 14, wherein said structural gene codes for a polypeptide that is toxic to insects and/or their larvae.

16. A method according to claim 15, wherein said polypeptide is a crystalline protein of *Bacillus thuringiensis*.

17. A method according to claim 16, wherein said crystalline protein is encoded by a synthetic B.t. gene.

18. A method according to claim 14, wherein said structural gene codes for a lytic peptide.

19. A method according to claim 14, wherein said structural gene codes for a pathogenesis related protein PRP.

20. A method according to claim 1, wherein the plant material to be transformed originates from a plant or viable parts thereof, that are in a state of competence for an Agrobacterium infection.

21. A method according to claim 20, wherein said viable parts thereof are selected from the group consisting of plant protoplasts, plant cell culture cells, cells in plant tissue, pollen, pollen tubes, egg-cells, embryo-sacs, zygotes, and embryos in different stages of development.

22. A method according to claim 20, wherein a plant is used that has reached the stage of development extending between seed germination and the 4-leaf stage.

23. A method according to claim 20, wherein a plant seedling is used which is germinated from an immature embryo.

24. A method according to claim 21, wherein said viable part is an immature developing embryo.

25. A method according to claim 1, wherein the infection of the plant material is accomplished by one of the methods selected from the group consisting of (a) artificially wounding the epidermal tissue and rubbing the microorganism-containing transforming suspension into the wounded tissue;

(b) incubating or co-cultivating the transfer microorganisms together with the wounded plant tissue or, alternatively, a plant protoplast; and (c) injecting the microorganism-containing transforming suspension into the plant material to be transformed.

26. A method according to claim 25, wherein the inoculation of the microorganism-containing transforming suspension is carried out preferably in regions of the plant or viable parts thereof that contain meristematic tissue.

27. A method according to claim 26, wherein the microorganism-containing transforming suspension is inoculated repeatedly into a meristematic tissue region of the plant or a viable parts thereof.

28. A method according to claim 25, wherein the inoculation of the microorganism-containing transforming suspension is effected in the boundary area between root and stem, the so-called root collar of planfiets already differentiated into stem, root and leaves.

29. A method according to claim 25, wherein the inoculation is effected in the immediate vicinity of the coleoptilar node of plant seedlings.

30. A method according to claim 25, wherein the inoculation is effected directly into the coleoptilar node of plant seedlings.

31. A method according to claim 25, wherein the inoculation is effected in meristematic tissue region of the coleoptilar node of plant seedlings after decapitation of the coleoptile tip.

32. A method according to claim 25, wherein the inoculation is effected by co-cultivating of shoots of plant seedlings germinated from immature embryos, with the microorganism-containing transforming suspension, said shoots being obtainable by germinating embryos on a suitable agar medium and isolating the developing shoots from the seedlings by cutting just below the coleoptilar node, where the shoot meristem is located.

33. A method according to claim 32, wherein the plant shoots are wounded artificially prior to the co-cultivation.

34. A method according to claim 25, wherein the concentration of the transfer microorgansim in the inoculation solution ranges from $10^5$ to $10^{10}$ organism per ml of inoculation solution.

35. A method according to claim 1, wherein the plant material to be transformed is from a dicotyledonous plant.

36. A method according to claim 1, wherein the plant material to be transformed is from a monocotyledonous plant.

37. A method according to claim 36, wherein the said monocotyledonous plant is a plant from the family Gramineae.

38. A method according to claim 37, wherein the the graminaccous plant is a plant from one of the following genera: Avena, Hordeum, Oryzae, Panicum, Saccharum, Secale, Setaria, Sorghum, Triticum, zea.

39. A method according to claim 36, wherein the transfer microorganisms to be inoculated are pretreated with a specific inducing composition comprising an exudate of a dicotyledonous plant.

40. A method according to claim 36, wherein the transfer microorganisms to be inoculated are pretreated with a specific inducing composition comprising at least one of the compounds of the formula I

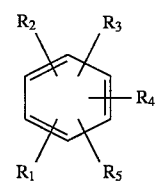

(I)

in which $R_1$, $R_2$, $R_3$, $R_4$ and $R_5$, independently of one another, each represents hydrogen or a substituent selected from the group comprising OH, COOH, CHO, COCH$_3$, OCH$_3$ and CH=CHCOOH, with the proviso that a minimum of one and a maximum of three of the radicals $R_1$ to $R_5$ represent hydrogen.

41. A method according to claim 40, wherein the inducing composition comprises at least one of the compounds of the following formula Ia

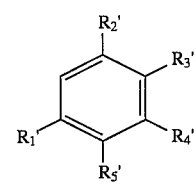

(Ia)

in which
$R_1'$ and $R_4'$, independently of one another, each represents H, OH or OCH$_3$;

$R_2'$ represents H, COOH, CHO, COCH$_3$ or CH=CHCOOH; and $R_3'$ and $R_5'$, independently of one another, each represents H or OH, with the proviso that a minimum of one and a maximum of three of the radicals $R_1'$, $R_2'$, $R_3'$, $R_4'$ and $R_5'$ represent hydrogen.

42. A method according to claim 40, wherein the inducing composition comprises at least one of the following compounds:

4-hydroxy-3,5-dimethoxyacetophenone,
4-hydroxy-3-methoxyacetophenone,
4-hydroxy-3,5-dimethoxybenzaldehyde,
4-hydroxy-3-methoxybenzaldehyde
4-hydroxy-3,5-dimethoxybenzoic acid,
3,4,5-trihydroxybenzoic acid,
3,4-dihydroxybenzoic acid,
2,4-dihydroxybenzoic acid,
β-hydroxybenzoic acid,
1,2,3-trihydroxybenzene and
1,2-dihydroxybenzene and
2-(3,5-dimethoxy-4-hydroxyphenyl)acrylic acid.

43. A method of immunizing plants against an undesired virus attack, wherein a DNA exhibiting a protective action against further viral infections is introduced into the said plant to be protected by a method according to claim 1.

* * * * *

UNITED STATES PATENT AND TRADEMARK OFFICE
CERTIFICATE OF CORRECTION

PATENT NO. : 5,569,597

DATED : October 29, 1996

INVENTOR(S) : Grimsley *et al.*

It is certified that error appears in the above-identified patent and that said Letters Patent is hereby corrected as shown below:

Column 2, line 29: "vital" should read --viral--;

line 31: "vital" should read --viral--.

Column 3, line 4: "vital" should read --viral--.

Column 4, line 34: "the plant its eft" should read --the plant itself--.

Column 6, line 6: "(pTitBo542, pEA1)" should read --(pTiBo542, pEA1)--;

line 9: "for the" should read --for the controlled transformation of plants or viable parts thereof.--.

Column 7, line 25: "vital" should read --viral--;

line 27: "vital" should read --viral--;

line 41: "vital" should read --viral--;

line 48: "vital" should read --viral--.

UNITED STATES PATENT AND TRADEMARK OFFICE
CERTIFICATE OF CORRECTION

PATENT NO. : 5,569,597

DATED : October 29, 1996

INVENTOR(S) : Grimsley *et al.*

It is certified that error appears in the above-identified patent and that said Letters Patent is hereby corrected as shown below:

Column 8, line 1: "vital" should read --viral--;

line 4: "vital" should read --viral--;

line 6: "vital" should read --viral--;

line 24: "vital" should read --viral--;

line 32: "vital" should read --viral--;

line 48: "Canlimo" should read --Caulimo--.

Column 9, line 62: "vital" should read --viral--.

Column 10, line 17: "swain" should read --strain--;

line 19: "trait" should read --unit--;

line 36: "pyrimidin" should read --pyrimidines--.

Column 11, line 1: "them are incorporated" should read --there are incorporated--;

line 63: "PR-O, PR-)', PR-4," should read --PR-O, PR-O', PR-4,--.

UNITED STATES PATENT AND TRADEMARK OFFICE
CERTIFICATE OF CORRECTION

PATENT NO. : 5,569,597

DATED : October 29, 1996

INVENTOR(S) : Grimsley et al.

It is certified that error appears in the above-identified patent and that said Letters Patent is hereby corrected as shown below:

Column 12, line 25: "somatostafin" should read --somatostatin--.

Column 13, line 14: "[Frank Get al (1980)]." should read --[Frank G et al. (1980)].--

Column 14, line 38: "chloramphcnicol" should read --chloramphenicol--;

line 42: "regularable" should read --regulatable--.

Column 15, line 38: "shuffle" should read --shuttle--;

Column 15, line 58: "role" should read --rule--.

Column 17, line 29: "graminaeeous" should read --graminaceous--.

Column 18, line 65: "mefistematic" should read --meristematic--.

Column 19, line 40: "meristemafic" should read --meristematic--.

Column 21, line 52: "Angiospermat" should read --*Angiospermae*--;

line 57: "Cornpositae" should read --*Compositae*--;

line 62: "Gramineae" should read --*Gramineae*--.

UNITED STATES PATENT AND TRADEMARK OFFICE
CERTIFICATE OF CORRECTION

PATENT NO. : 5,569,597
DATED : October 29, 1996
INVENTOR(S) : Grimsley et al.

Page 4 of 9

It is certified that error appears in the above-identified patent and that said Letters Patent is hereby corrected as shown below:

Column 22, line 4: "Aractis" should read --*Arachis*--;

lines 13-14: "Monocotyledoneat" should read -- *Monocotyledoneae* --;

line 33: "Alliaceat" should read --*Alliaceae*--;

line 34: "Bromeliaceae, Gramineat, Liliaceat" should read --*Bromeliaceae, Gramineae, Liliaceae*--;

line 43: "Aliium" should read --*Allium*--;

line 44: "Saccharin" should read --*Saccharum*--;

line 49: "Gramineat" should read --*Gramineae*--;

line 60: "graminaeeous" should read --graminaceous--.

Column 23, line 31: "vital" should read --viral--;

line 34: "vital" should read --viral--;

line 37: "vital" should read --viral--.

UNITED STATES PATENT AND TRADEMARK OFFICE
CERTIFICATE OF CORRECTION

PATENT NO. : 5,569,597

DATED : October 29, 1996

INVENTOR(S) : Grimsley *et al.*

It is certified that error appears in the above-identified patent and that said Letters Patent is hereby corrected as shown below:

Column 24, line 14: "vital" should read --viral--;

line 18: "vital" should read --viral--.

Column 25, line 4: "Maniafis" should read --Maniatis--;

line 51: "phosphatasc" should read --phosphatase--.

Column 26, line 7: "Manialls" should read --Maniatis--;

line 11: "Maniaus" should read --Maniatis--;

line 30: "citmte" should read --citrate--;

line 67: "Maniails" should read --Maniatis--.

Column 27, line 31: "pV 118be" should read --pV118bc--;

line 31: "BstEH" should read --BstEII--;

line 66: "[Leeroans J." should read --[Leemans J.--.

Column 28, line 31: "oventight" should read --overnight--.

UNITED STATES PATENT AND TRADEMARK OFFICE
CERTIFICATE OF CORRECTION

PATENT NO. : 5,569,597

DATED : October 29, 1996

INVENTOR(S) : Grimsley et al.

It is certified that error appears in the above-identified patent and that said Letters Patent is hereby corrected as shown below:

Column 29, line 44: "embryos arc" should read --embryos are--;

line 47: "Instimt" should read --Institut--.

Column 30, line 6: "arc cloned" should read --are cloned--;

line 8: "lincarised" should read --linearised--;

line 13: "lincarised" should read --linearised--;

line 28: "(inservector)." should read --(inser:vector).--;

line 29: "shutfie" should read --shuttle--;

line 30: "smbly" should read --stably--;

line 38: "[An Get al, 1985]." should read --[An G *et al*, 1985].;

line 58: "hybridisafion" should read --hybridisation--;

line 66: "Agrobaeterium" should read --*Agrobacterium*--.

Column 31, line 3: "tetraeycline" should read --tetracycline--;

line 4: "dimefie" should read --dimeric--;

UNITED STATES PATENT AND TRADEMARK OFFICE
CERTIFICATE OF CORRECTION

PATENT NO. : 5,569,597

DATED : October 29, 1996

INVENTOR(S) : Grimsley et al.

It is certified that error appears in the above-identified patent and that said Letters Patent is hereby corrected as shown below:

Column 31, line 12: "fonowing" should read --following--;

line 46: "cosmic" should read --cosmid--;

line 57: "Sat I-Bst EH" should read --Sal I-Bst EII--.

Column 32, line 18: "A 1.6 met" should read --A 1.6 mer--;

line 43: "Beyan" should read --Bevan--;

line 45: "0relation to" should read --relation to--;

line 53: "compelend" should read --competend-;

line 56: "(X-gat)," should read --(X-gal),--;

line 58: "MSV-insen" should read --MSV-insert--.

Column 33, line 19: "abom" should read --a bom--.

Column 34, line 36: "stefilisation" should read --sterilisation--;

line 48: "peri dishes" should read --petri dishes--;

line 67: "rain" should read --min--.

UNITED STATES PATENT AND TRADEMARK OFFICE
CERTIFICATE OF CORRECTION

PATENT NO. : 5,569,597

DATED : October 29, 1996

INVENTOR(S) : Grimsley *et al.*

It is certified that error appears in the above-identified patent and that said Letters Patent is hereby corrected as shown below:

Column 36, line 14: "coleopfile" should read --coleoptile--;

line 23: "scumliar node" should read --scutellar node--;

line 42: "coleopfile" should read --coleoptile--;

line 64: "$\mu$lass" should read --glass--.

Column 37, line 8: "apicai" should read --apical--;

line 15: "planfiets" should read --plantlets-- ;

line 33: "robe" should read --tube--;

line 35: "discarried" should read --discarded--.

Column 38, line 51: "DH5ot and" should read --DH5$\alpha$ and--.

Column 39, line 3: "cells/mi" should read --cells/ml--;

line 37: "glucurpmode (X-Gluc)" should read --glucuronide (X-Gluc)--.

Column 45, line 51: "Sambrook Jet al," should read --Sambrook J *et al*,--;

line 59: "Stachei et al," should read --Stachel *et al*,--.

UNITED STATES PATENT AND TRADEMARK OFFICE
CERTIFICATE OF CORRECTION

PATENT NO. : 5,569,597

DATED : October 29, 1996

INVENTOR(S) : Grimsley *et al.*

It is certified that error appears in the above-identified patent and that said Letters Patent is hereby corrected as shown below:

Column 47, line 63, claim 28: "planfiets" should read --plantlets--.

Column 48, line 29, claim 38: "graminaccous" should read --graminaceous--.

Signed and Sealed this

Seventeenth Day of March, 1998

Attest:

BRUCE LEHMAN

Attesting Officer

Commissioner of Patents and Trademarks